United States Patent
Pei et al.

(10) Patent No.: US 11,643,428 B2
(45) Date of Patent: May 9, 2023

(54) THERAPEUTIC DRUG FOR NEURODEGENERATIVE DISEASE AND APPLICATION THEREOF

(71) Applicant: SHANGHAI PHARMACEUTICALS HOLDING CO., LTD., Shanghai (CN)

(72) Inventors: Gang Pei, Shanghai (CN); Biao Yu, Shanghai (CN); Shichao Huang, Shanghai (CN); Xin Cao, Shanghai (CN); Fuchun Shi, Shanghai (CN); Yue Zhou, Shanghai (CN); Yuqian An, Shanghai (CN); Jing Lu, Shanghai (CN)

(73) Assignee: Shanghai Pharmaceuticals Holding Co., Ltd., Shanghai (CN)

( * ) Notice: Subject to any disclaimer, the term of this patent is extended or adjusted under 35 U.S.C. 154(b) by 0 days.

(21) Appl. No.: 16/967,584

(22) PCT Filed: Jan. 29, 2019

(86) PCT No.: PCT/CN2019/073773
§ 371 (c)(1),
(2) Date: Aug. 5, 2020

(87) PCT Pub. No.: WO2019/154195
PCT Pub. Date: Aug. 15, 2019

(65) Prior Publication Data
US 2021/0087214 A1    Mar. 25, 2021

(30) Foreign Application Priority Data

Feb. 6, 2018  (CN) .......................... 201810119279.3
Jun. 14, 2018  (CN) .......................... 201810616404.1

(51) Int. Cl.
| | |
|---|---|
| *C07H 1/00* | (2006.01) |
| *C07H 5/06* | (2006.01) |
| *A61P 25/28* | (2006.01) |
| *C07H 13/04* | (2006.01) |

(52) U.S. Cl.
CPC .............. *C07H 13/04* (2013.01); *A61P 25/28* (2018.01); *C07H 1/00* (2013.01); *C07H 5/06* (2013.01)

(58) Field of Classification Search
None
See application file for complete search history.

(56) References Cited

U.S. PATENT DOCUMENTS

2019/0177354 A1  6/2019  Yao et al.

FOREIGN PATENT DOCUMENTS

| CN | 101914595 A | 12/2010 |
|---|---|---|
| CN | 104231013 A | 12/2014 |
| CN | 104958287 A | 10/2015 |
| CN | 105906672 | 8/2016 |
| EP | 3450444 A1 | 3/2019 |
| JP | 2005272355 A | 10/2005 |
| JP | 2017043563 A | 3/2017 |
| WO | 2006138418 A2 | 12/2006 |
| WO | 20119093007 A1 | 7/2009 |

OTHER PUBLICATIONS

Wolff, Manfred E. "Burger's Medicinal Chemistry, 5ed, Part I", John Wiley & Sons, 1995, pp. 975-977 (Year: 1995).*
Banker, G.S. et al, "Modern Pharmaceutics, 3ed.", Marcel Dekker, New York, 1996, p. 596 (Year: 1996).*
Grond et al., European Journal of Organic Chemistry, 2000, vol. 10, pp. 1875-1881 (Year: 2000).*
International Search Report issued in International Patent Application No. PCT/CN2019/073773, dated Apr. 29, 2019.
Written Opinion of the International Searching Authority issued in International Patent Application No. PCT/CN2019/073773, dated Apr. 29, 2019.
Search Report issued in Chinese Patent Application No. 201910089011.4, dated Apr. 14, 2020.
Chinese 1st Office Action issued in Chinese Patent Application No. 201910089011.4, dated Apr. 27, 2020.
Chinese 2nd Office Action issued in Chinese Patent Application No. 201910089011.4, dated Jul. 1, 2020.
Stephanie Grond et al., Studies of Precursor-Directed Biosynthesis with Streptomyces, Structural Diversity of 1-O-Acyl α-L-Rhamnopyranosides by Precursor-Directed Biosynthesis with Streptomyces griseoviridis, Eur. J. Org. Chem. May 2000, pp. 1875-1881, vol. 10.
Stephanie Grond et al., Novel α-L-Rhamnopyranosides from a Single Strain of Streptomyces by Supplement-Induced Biosynthetic Steps, Eur. J. Org. Chem. Sep. 2002, pp. 3237-3242, vol. 19.
Yu Miao et al., Design, synthesis and LPS induced N9 microglia cell activation inhibitory effects of novel ferulic acid derivatives, Chinese Journal of Medicinal Chemistry. vol. 24—issue 4, pp. 293-297, 2014.
Extended European Search Report dated Oct. 11, 2021, issued in European Patent Application No. 19751440.9.
1st Office Action dated Nov. 25, 2021, issued in India Patent Application No. 202047036786.
Sultana Rukhsana, "Ferulic acid ethyl ester as a potential therapy in neurodegenerative disorders", Biochimica et Biophysica Acta. Molecular Basis of Disease., May 1, 2012 (May 1, 2012), pp. 748-752, vol. 1822, No. 5.

(Continued)

*Primary Examiner* — Traviss C McIntosh, III
(74) *Attorney, Agent, or Firm* — Pilloff Passino & Cosenza LLP; Sean A. Passino; Rachel K. Pilloff

(57) ABSTRACT

The present invention relates to a novel therapeutic drug for a neurodegenerative disease and an application thereof. Provided is a novel compound of formula (I). The compound can effectively facilitate the proliferation of neural stem cells in both in vitro and in vivo experiments and can be used as a treatment approach for facilitating neuroregeneration to fight against cognitive decline associated with aging or a neurodegenerative disease.

19 Claims, 16 Drawing Sheets

(56) References Cited

OTHER PUBLICATIONS

Allisson B Justino et al: "Peel of araticum fruit (Annona crassiflora Mart.) as a source of antioxidant compounds with [alpha]-amylase, [alpha]-glucosidase and glycation inhibitory activities", Bioorganic Chemistry, Academic Press Inc., Nov. 9, 2016 (Nov. 9, 2016), pp. 167-182, vol. 69, New York, NY, US.
Josh Lee Hixson et al, "Hydroxycinnamoyl Glucose and Tartrate Esters and Their Role in the Formation of Ethylphenols in Wine", Journal of Agricultural and Food Chemistry, Dec. 5, 2016 (Dec. 5, 2016), pp. 9401-9411, vol. 64, No. 49.
Japanese Office Action issued in Japanese Patent Application No. 2020564302, dated Nov. 22, 2022.
Liuqiang Zhang et al., "Two new phenylpropanoid glycosides with interesterification from Scrophularia dentata Royle ex Benth," Journal of Molecular Structure, Jun. 2013, pp. 299-302, vol. 1049.
Ji-Jing Yan et al., "Protection against beta-amyloid peptide toxicity in vivo with long-term administration of ferulic acid," British Journal of Pharmacology, May 2001, pp. 89-96, vol. 133.

\* cited by examiner

THERAPEUTIC DRUG FOR NEURODEGENERATIVE DISEASE AND APPLICATION THEREOF

TECHNICAL FIELD

The present invention relates to the field of pharmacy, and more particularly, to novel therapeutic drugs for neurodegenerative diseases and applications thereof.

BACKGROUND

Neurodegenerative diseases refer to a generic term of a group of diseases caused by chronic progressive neurodegeneration of central nervous tissue. These diseases include Parkinson's disease (PD), Alzheimer's disease (AD), Huntington disease (HD), amyotrophic lateral sclerosis (ALS), etc.

Alzheimer's disease, also known as presenile dementia, is a chronic progressive neurodegenerative disease characterized by progressive decline in memory ability, cognitive dysfunction and loss of independent self-care ability. With the increasing in aging population, the incidence of AD is increasing year by year and AD has become the most important public concern about health issues.

AD pathology is primarily characterized by the presence of amyloid plaques and neurofibrillary tangles. Amyloid plaques are the characteristics of pathological change for Alzheimer's disease, and are mainly formed by the extracellular accumulation of amyloid beta (Aβ) protein which are produced abnormally in cells in a large number. Currently, there are a number of theories which try to explain the pathogenic mechanism of amyloid plaques. "As hypothesis" proposed by Hardy and Selkoe is a widely accepted theory. This theory believes that under the long-term effect of complex genetic and environmental factors, nerve cells produce abnormally large amounts of Aβ, which accumulates to form oligomers and amyloid plaques. Via a series of cascade reactions (including free radical reaction, mitochondrial oxidative damage, inflammatory response, etc.), Aβs (in particular, oligomerized Aβs) directly or indirectly act on neurons and glial cells, leading to synaptic dysfunction and neuronal damage and activating microglial cells and astrocyte cells, which accelerates the formation of neurofibrillary tangles and leads to cognitive impairment after long-term effect. Recently, a large number of studies provides various evidences to support the "Aβ hypothesis", suggesting the central role of Aβ in the pathogenesis of Alzheimer's disease.

Parkinson's disease is a common neurodegenerative disease. Clinically, it mainly manifests as symptoms such as slow response, tremor, body stiffness and further imbalance. Studies on the brain tissue of PD patients showed that the dopaminergic neurons in substantia nigra of the brain were lost in patients with this disease. Lewy bodies are one of the landmark lesions of degenerative neurons in Parkinson's disease. Studies have shown that Lewy bodies are formed in the brain tissues of patients with various neurodegenerative diseases, including Alzheimer's disease, Parkinson's disease, DLB disease (Dementia with Lewy Body), etc. Further, some research results support that the transplantation of neural stem cells may contribute to the treatment of Huntington disease and amyotrophic lateral sclerosis.

In the mammalian brain, the proliferation and self-renewal of neural stem cells (Neural Progenitor Cells, NPC) continue throughout the whole life, which is an important for neurogenesis. In the context of aging, long-term stress and nervous system diseases, such as Alzheimer's disease (AD), the proliferation and self-renewal ability of neural stem cells decrease, leading to impairment of cognitive function. Facilitating neuroregeneration is considered to be a potential treatment approach to fight against aging and aging-related neurodegenerative diseases. Therefore, one possible solution is to transplant embryonic neural stem cells or neural stem cells induced in vitro for cell replacement therapy. However, there is still some controversy about this newly created complex technology, especially the safety issues and the sources of these cells, etc. Another solution is to activate endogenous neural stem cells by a pharmacological means, thereby achieving the purpose of treating a neurodegenerative disease. Pharmacological means is easy to operate and can specifically target the specific functions of neural stem cells, and therefore, the activation of endogenous neural stem cells is not only a feasible treatment approach but can also be used as a prevention approach. However, those skilled in the art still need to find suitable medicament which can better cross in-vivo barriers to effectively activate endogenous neural stem cells, so as to achieve effective treatment.

Filed of the Present Invention

An object of the present invention is to provide novel therapeutic drugs for a neurodegenerative diseases and applications thereof.

The first aspect of the present invention provided is a compound of formula (I) or an isomer, a solvate or a precursor thereof, or their pharmaceutically acceptable salts,

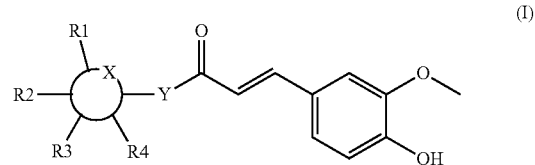

wherein

a six-membered heterocyclic ring, and X is O;

Y is independently selected from O and N;

when Y represents O, the compound is in β configuration or is a mixture of α configuration and β configuration in any ratio; and when Y represents N, the compound is in α configuration, β configuration or is a mixture of α configuration and β configuration in any ratio.

R1 to R4 are each independently selected from hydrogen, hydroxyl, C1 to C4 alkyl, C2 to C4 alkenyl, C2 to C4 alkynyl and halogen, or two adjacent groups in R1 to R4 are connected with each other to form a ring structure together with the parent ring.

In a preferred embodiment, in the compound of formula (I) or an isomer, a solvate or a precursor thereof, or their pharmaceutically acceptable salts, R1 to R4 are each independently selected from hydrogen, hydroxyl and C1-C2 alkyl.

In another preferred embodiment, the compound includes

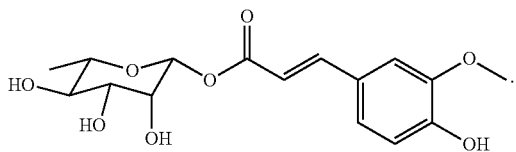

In another preferred embodiment, the compound includes

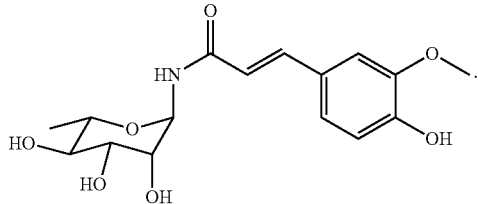

In another referred embodiment, the compound includes

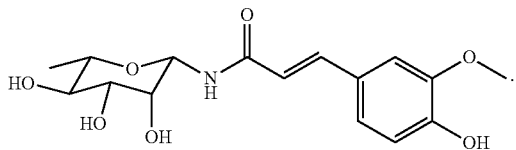

In another preferred embodiment, the compound does not include

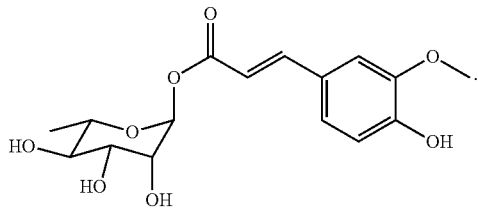

In another aspect of the present invention, provided is the use of the compound of formula (I) or an isomer, a solvate or a precursor thereof, or their pharmaceutically acceptable salts in the manufacture of a medicament or a medicine kit for preventing, alleviating or treating neurodegenarative diseases, depression or stroke.

In a preferred embodiment, the neurodegenerative diseases are:

neurodegenerative diseases characterized by the occurrence of neuroinflammation in the brain; or neurodegenerative diseases characterized by a significant increase in Aβ production; or neurodegenerative diseases characterized by a significant decline in learning and memory ability; or the neurodegenerative disease characterized by a decline in function of neural stem cells; or neurodegenarative diseases characterized by a decline in motor coordination ability; or neurodegenerative diseases characterized by a decrease in the number of dopaminergic neurons in substantia nigra; or neurodegenerative diseases characterized by a decrease in the level of striatal dopaminergic nerve fibers.

In another preferred embodiment, the occurrence of neuroinflammation in the brain is characterized by a significant increase in the expression of inflammatory factors; the inflammatory factors are, for example, TNF-α and 1L-1β.

In another preferred embodiment, the neurodegenerative diseases include Alzheimer's disease, Parkinson's disease, dementia with Lewy bodies (DLB), Huntington disease and amyotrophic lateral sclerosis.

In another aspect of the present invention, provided is the use of the compound of formula (I) or an isomer, a solvate or a precursor thereof, or their pharmaceutically acceptable salts in the manufacture of a composition, a kit or a medicine kit for inhibiting neuroinflammation.

In another aspect of the present invention, provided is the use of the compound of formula (I) or an isomer, a solvate or a precursor thereof, or their pharmaceutically acceptable salts in the manufacture of a composition, a kit or a medicine kit for improving the function of neural stem cells.

In another aspect of the present invention, provided is the use of the compound of formula (I) or an isomer, a solvate or a precursor thereof, or their pharmaceutically acceptable salts in the manufacture of a composition, a kit or a medicine kit for decreasing Aβ production.

In another aspect of the present invention, provided is the use of the compound of formula (I) or an isomer, a solvate or a precursor thereof, or their pharmaceutically acceptable salts in the manufacture of a composition, a kit or a medicine kit for increasing the number of dopaminergic neurons in substantia nigra.

In another aspect of the present invention, provided is the use of the compound of formula (I) or an isomer, a solvate or a precursor thereof, or their pharmaceutically acceptable salts in the manufacture of a composition, a kit or a medicine kit for increasing the level of striatal dopaminergic nerve fibers.

In a preferred embodiment, the compound includes:

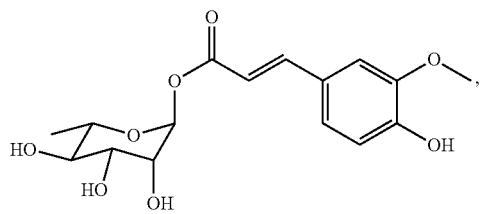

also known as PL201;

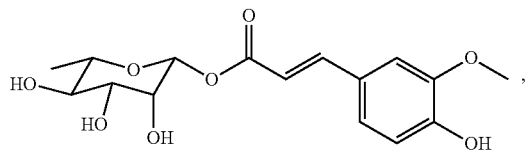 [SMILES: COc1cc(/C=C/C(=O)OC2OC(C)C(O)C(O)C2O)ccc1O]

also known as PL202;

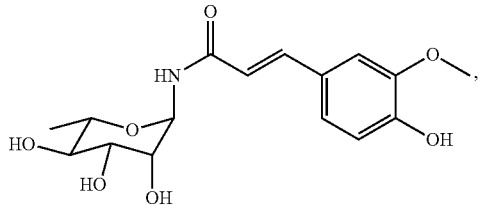

also known as PL172; and

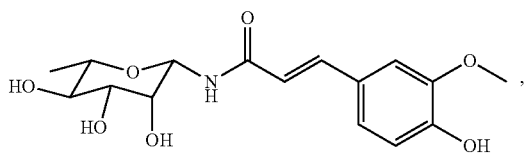 [SMILES: COc1cc(/C=C/C(=O)NC2OC(C)C(O)C(O)C2O)ccc1O]

also known as PL171.

In another aspect of the present invention, provided is a pharmaceutical composition, the pharmaceutical composition comprising: the compound of formula (I) or an isomer, a solvate or a precursor thereof, or their pharmaceutically acceptable salts; and a pharmaceutically acceptable carrier.

In a preferred embodiment, the compound of formula (I) or an isomer, a solvate or a precursor thereof, or their pharmaceutically acceptable salts is in an effective amount in a pharmaceutical composition; preferably, the effective amount is 0.01%-50% by weight, such as, but not limited to, 0.01%-5%, 0.03%-3%, 0.05%-1%, 20%-30%, and 40%-50% by weight; more preferably 0.03%-30% by weight; even more preferably, 0.05%-10% by weight.

In another aspect of the present invention, the dosage form of the pharmaceutical composition provided includes a powder, a pulvis, a tablet, a pill, a capsule, a sustained-release preparation, a controlled-release preparation, an injection, an infusion liquid and a suspension.

In another aspect of the present invention, provided is a medicine kit, wherein the medicine kit comprises: the compound of formula (I) or an isomer, a solvate or a precursor thereof, or their pharmaceutically acceptable salts; or the pharmaceutical composition.

In another aspect of the present invention, provided is a method for preventing, alleviating or treating neurodegenerative diseases, depression or stroke, wherein the method comprises: administering to a subject in need thereof an effective amount of the compound of formula (I) or an isomer, a solvate or a precursor thereof or their pharmaceutically acceptable salts.

In another aspect of the present invention, provided is a method for preparing the compound of formula III, IV or V, the method comprising the step of: reacting β-rhamnoside, α-1-aminorhamnoside or β-1-aminorhamnoside with tetrabutyl ammonium fluoride respectively, to obtain the compounds of formula III to V with the following structures:

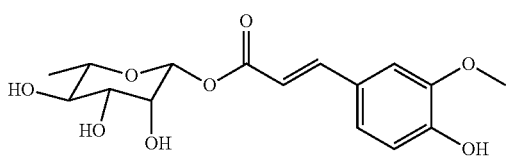

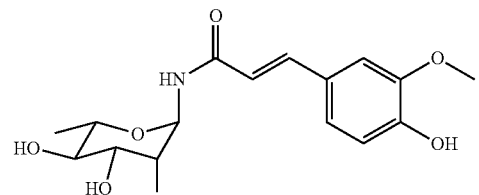

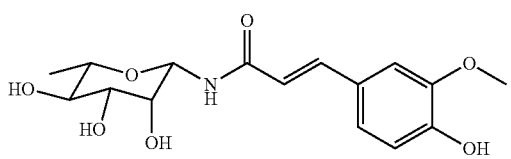

In another preferred embodiment, the β-rhamnoside is obtained by reacting 2,3,4-O-triacetyl rhamnose with (4-O-tert-butyldimethylsilyl)-ferulic acid acyl chloride.

In another preferred embodiment, the α-1-aminorhamnoside and/or the β-1-aminorhamnoside is obtained by reacting 2,3,4-O-triacetyl-1-aminorhamnose with (4-O-tert-butyldimethylsilyl)-ferulic acid acyl chloride.

Other aspects of the invention would have been obvious to those skilled in the art due to the contents disclosed herein.

DETAILED DESCRIPTION OF THE PREFERRED EMBODIMENT

Figure 1:
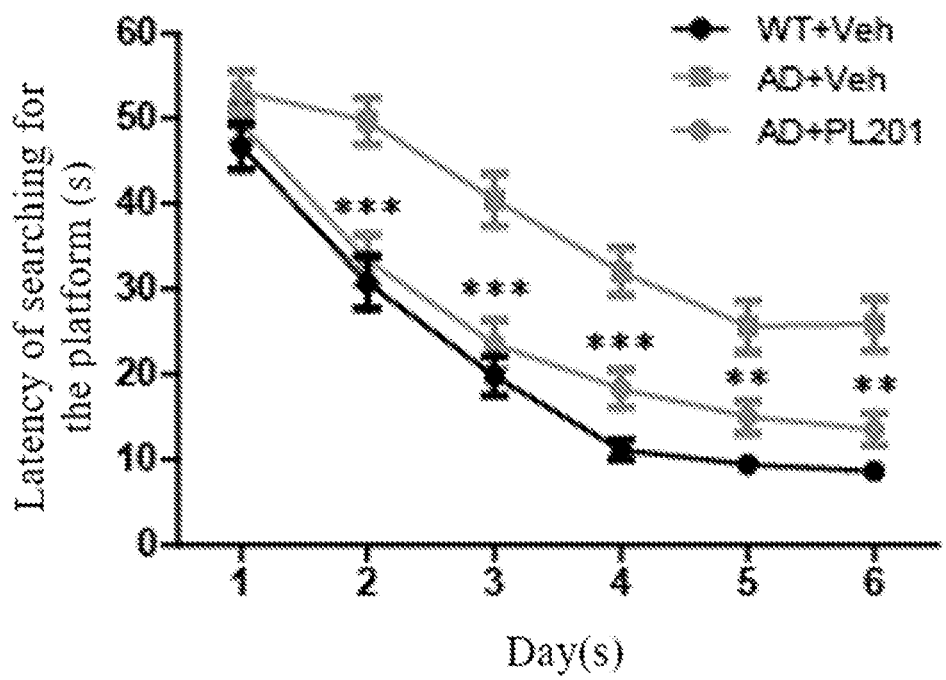
FIG. 1. PL201 improves the indicator for Morris water maze test of AD mouse.

After extensive research, the inventors have found that the compound of formula (I) can significantly relieve the symptoms of neurodegenerative diseases. In both in vitro and in vivo experiments, the compound of formula (I) can effectively enhance the function of neural stem cells. The compound of formula (I) not only can prevent, but also can be used as a treatment approach for facilitating neuroregeneration to fight against cognitive decline associated with aging or a neurodegenerative disease.

Terms

The term "alkyl" as used herein refers to linear or branched, saturated aliphatic hydrocarbon groups containing 1 to 4 carbon atoms (preferably 1 to 2 carbon atoms). For example, alkyl includes but is not limited to methyl, ethyl, n-propyl, isopropyl, n-butyl, isobutyl, and t-butyl.

The term "alkenyl" as used herein includes linear or branched hydrocarbon groups containing at least one carbon-carbon double bond and 2 to 4 carbon atoms (preferably 2 to 3 carbon atoms).

The term "alkynyl" as used herein includes linear or branched hydrocarbon groups containing at least one carbon-carbon triple bond and 2 to 4 carbon atoms (preferably 2 to 3 carbon atoms).

The term "halogen" as used herein refers to F, Cl, Br, or I.

The term "isomer" as used herein includes geometric isomer, enantiomers and diastereomers (such as cis-trans isomer and conformational isomer).

The expressing method of

as used herein is well-known to a person skilled in the art, which represents one heterocycle having an atom X. In a preferred embodiment of the present invention, the

is a six-membered heterocyclic ring.

The expressing method of

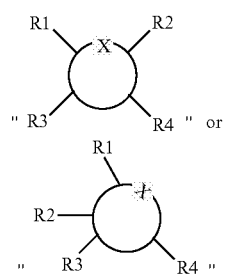

as used herein is well-known to a person skilled in the art, which represents the ring with any one or more positions which can be substituted by optional R1 to R4 substitutions. Moreover, the substitutions may be different at different substitution positions.

The term "solvate" as used herein represents the compound carrying a solvent molecule, for example, the solvate may be a hydrate.

In the present invention, the term "contain/contains/containing/contained" represents that various ingredients can be applied together to the mixture or composition of the present invention. Therefore, the term "substantially consist of" and "consist of" are encompassed by the term "contain".

In the present invention, a "pharmaceutically acceptable" component is the substance suitable for human and/or animal without excessive adverse side effects (such as toxicity, irritation and allergy), i.e., with a reasonable benefit/risk ratio.

In the present invention, a "pharmaceutically acceptable carrier" is a pharmaceutical or food acceptable solvent, suspension agent or excipient used to deliver the compound of formula (I), an isomer, a solvate, a precursor thereof, or their pharmaceutically acceptable salts of the present invention, to animals or humans. The carrier can be a liquid or a solid.

Compound

The present invention firstly provides a compound as shown in structural formula (I):

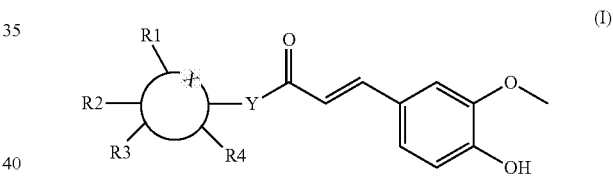

It should be understood that the position of X in formula (I) is an illustrative position, which is not limited to one side of R1 in the formula (the position between R1 and the

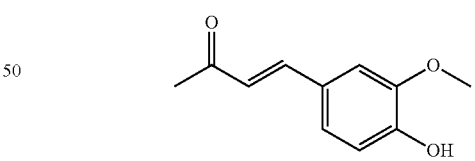

group), but can also exist between R1 and R2, between R2 and R3, between R3 and R4, and between R4 and the

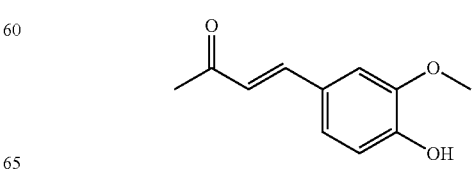

group, for example, the compound can also be:

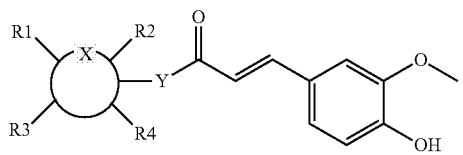

wherein

is a six-membered heterocyclic ring, and X is O; Y is independently selected from O and N; when Y represents O, the compound is in β configuration or is a mixture of a configuration and β configuration in any ratio; and when Y represents N, the compound is in a configuration, β configuration or is a mixture of a configuration and a configuration in any ratio; R1 to R4 are each independently selected from hydrogen, hydroxyl, C1-C4 alkyl, C2-C4 alkenyl, C2-C4 alkynyl, halogen, or two adjacent groups in R1 to R4 are connected with each other to form a ring structure (which can be a ring structure containing O) together with the parent ring.

As a preferred embodiment of the present invention, R1 to R4 are each independently selected from hydrogen, hydroxyl and C1-C2 alkyl.

The present invention further includes an isomer, a solvate, a precursor of the above-mentioned compound of formula (I), or their pharmaceutically acceptable salts, as long as they have the same or substantially the same function to that of the compound of formula (I). The "pharmaceutically acceptable salts" refer to salts produced by the reaction of the compound with an inorganic acid, an organic acid, an alkali metal or an alkaline earth metal. These salts include but are not limited to: (1) salts formed with inorganic acids such as hydrochloric acid, sulfuric acid, nitric acid and phosphoric acid; (2) salts formed with organic acids such as acetic acid, oxalic acid, succinic acid, tartaric acid, methanesulfonic acid, maleic acid, and arginine. Other salts include salts formed with alkali metals or alkaline earth metals (such as sodium, potassium, calcium or magnesium) in the form of esters, carbamates, or other conventional "prodrugs". Compounds have one or more asymmetric centers. Therefore, these compounds can exist as racemic mixtures, individual enantiomers, individual diastereomers, mixtures of diastereomers, or cis or trans isomers.

The "precursor of a compound" refers to a compound which, after being administered to a patient in an appropriate method, undergoes metabolic or chemical reactions in the patient to be converted into the compound of structural formula (I) or a salt or a solution composed of a compound of structural formula (I).

As a preferred embodiment of the present invention, the compound comprises the compounds as shown in formula II (PL201), formula III (PL202), formula IV (PL172) and formula V (PL171). The compounds of formula III and formula V are particularly preferred.

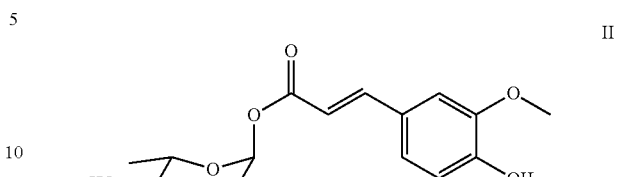

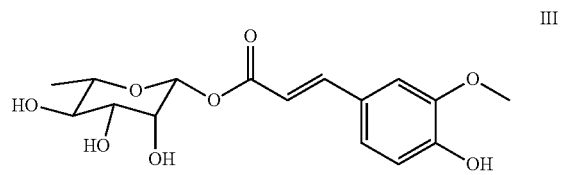

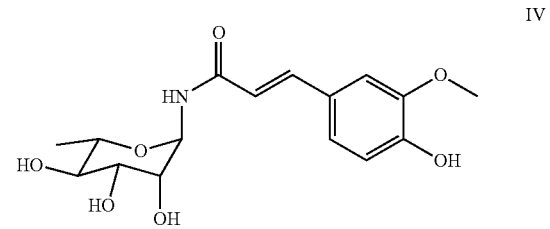

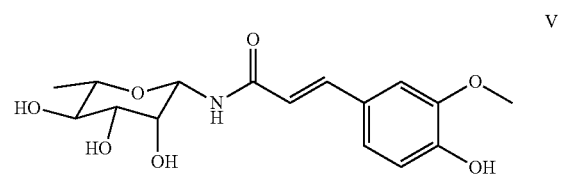

The compound of formula II is (α-L-rhamnopyranosyl) ferulic acid ester, including but not limited to,

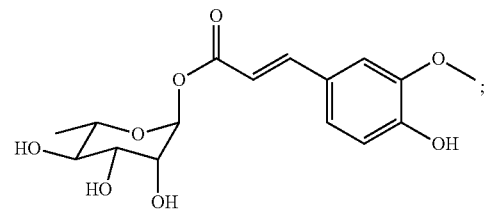 [SMILES: COc1cc(/C=C/C(=O)OC2OC(C)C(O)C(O)C2O)ccc1O]

the compound of formula III is (β-L-rhamnopyranosyl) ferulic acid ester, including but not limited to,

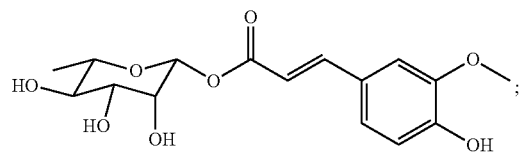 [SMILES: COc1cc(/C=C/C(=O)OC2OC(C)C(O)C(O)C2O)ccc1O]

the compound of formula IV is (1-amino-α-L-rhamnopyranosyl) ferulamide, including but not limited to,

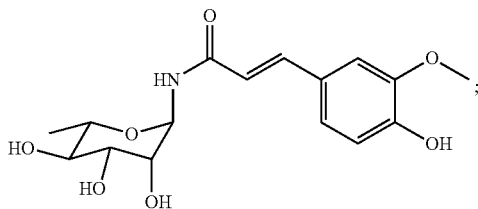 [SMILES: COc1cc(/C=C/C(=O)NC2OC(C)C(O)C(O)C2O)ccc1O]

and
the compound of formula V is (1-amino-β-L-rhamnopyranosyl) ferulamide, including but not limited to,

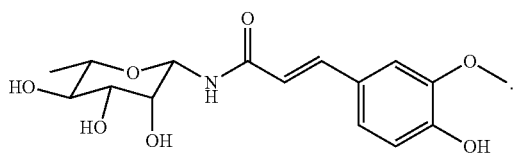 [SMILES: COc1cc(/C=C/C(=O)NC2OC(C)C(O)C(O)C2O)ccc1O]

In an embodiment of the present invention, the method for preparing a compound of formula III comprises the following steps:
Step 1, 2,3,4-O-triacetyl rhamnose and (4-O-tert-butyldimethylsilyl)-ferulic acid acyl chloride were mixed for reacting to obtain β glycosylation product having the structure as shown in formula VI;
Step 2, the β glycosylation product having the structure as shown in formula VI and tetra-butyl ammonium fluoride were mixed to obtain a tert-butyldimethylsilyl (TBS) deprotected product; and
Step 3, the tert-butyldimethylsilyl (TBS) deprotected product was hydrolyzed to obtain a compound of formula III

VI

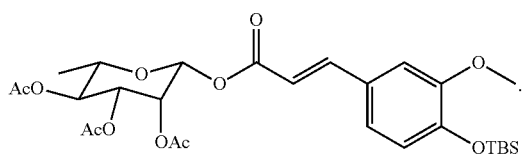

In an embodiment of the present invention, in step 1 herein above, 2,3,4-O-triacetyl rhamnose in an ice bath was added dropwise into (4-O-tert-butyldimethylsilyl)-ferulic acid acyl chloride.
In an embodiment of the present invention, the reaction of step 1 herein above was carried out at room temperature. The room temperature is 10° C.-40° C., preferably 15° C.-30° C., more preferably 20° C.-25° C.
In an embodiment of the present invention, step 1 herein above further includes the operations of obtaining α- and β glycosylation products respectively via column chromatography.
In an embodiment of the present invention, in step 2 herein above, the mixing was performed by adding tetra-butyl ammonium fluoride
dropwise into β glycosylation product at room temperature.

In an embodiment of the present invention, the method for preparing a compound of formula IV comprises the following steps:
Step 1, 1-amino-2,3,4-O-triacetyl rhamnose and (4-O-tert-butyldimethylsilyl)-ferulic acid acyl chloride were mixed for reacting to obtain α glycosylation product having the structure as shown in formula VIII;
Step 2, the α glycosylation product having the structure as shown in formula VIII and tetra-butyl ammonium fluoride were mixed to obtain α tert-butyldimethylsilyl (TBS) deprotected product; and
Step 3, the α tert-butyldimethylsilyl (TBS) deprotected product was hydrolyzed to obtain a compound of formula IV

VIII

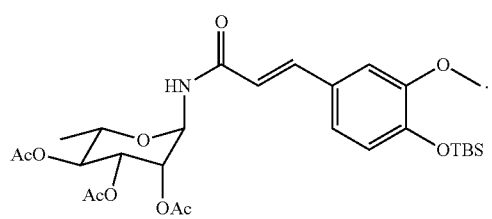

In an embodiment of the present invention, in step 1 herein above, 1-amino-2,3,4-O-triacetyl rhamnose in an ice bath was added dropwise into (4-O-tert-butyldimethylsilyl)-ferulic acid acyl chloride.
In an embodiment of the present invention, the reaction of step 1 herein above was carried out at room temperature. The room temperature is 10° C.-40° C., preferably 15° C.-30° C., more preferably 20° C.-25° C.
In an embodiment of the present invention, step 1 herein above further includes the operation of obtaining α glycosylation product via column chromatography.
In an embodiment of the present invention, in step 2 herein above, the mixing was performed by adding tetra-butyl ammonium fluoride
dropwise into α glycosylation product at room temperature.
In an embodiment of the present invention, the method for preparing a compound of formula V comprises the following steps:
Step 1, 1-amino-2,3,4-O-triacetyl rhamnose and (4-O-tert-butyldimethylsilyl)-ferulic acid acyl chloride were mixed for reacting to obtain β glycosylation product having the structure as shown in formula IX;
Step 2, the β glycosylation product having the structure as shown in formula IX and tetra-butyl ammonium fluoride were mixed to obtain β tert-butyldimethylsilyl (TBS) deprotected product; and
Step 3, the β tert-butyldimethylsilyl (TBS) deprotected product was hydrolyzed to obtain a compound of formula V

IX

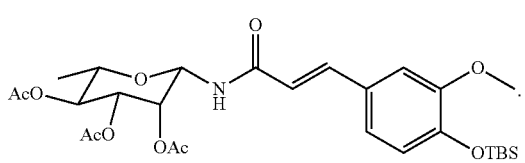

In an embodiment of the present invention, in step 1 herein above, 1-amino-2,3,4-O-triacetyl rhamnose in an ice bath was added dropwise into (4-O-tert-butyldimethylsilyl)-ferulic acid acyl chloride.

In an embodiment of the present invention, the reaction of step 1 herein above was carried out at room temperature. The room temperature is 10° C.-40° C., preferably 15° C.-30° C., more preferably 20° C.-25° C.

In an embodiment of the present invention, step 1 herein above further includes the operation of obtaining β glycosylation product via column chromatography.

In an embodiment of the present invention, in step 2 herein above, the mixing was performed by adding tetrabutyl ammonium fluoride dropwise into β glycosylation product at room temperature.

A person skilled in the art should understand that after knowing the structure of the compounds of the present invention, the compounds of the present invention can be obtained by a variety of methods well known in the art and using well known raw materials, such as methods of chemical synthesis or extraction from organisms (such as animals or plants), and these methods are encompassed by the present invention.

The synthesized compound can be further purified by column chromatography and high-performance liquid chromatography, etc.

Use

The inventors have found in studies that the compound of formula (I) of the present invention can significantly relieve the symptoms of neurodegenerative diseases. The compound of the present invention can inhibit neuroinflammation, reduce Aβ production, and enhance the functions of neural stem cells and dopaminergic neurons. After experimental demonstration, the compound of the present invention has significantly improved the learning and memory abilities of animals. According to the action mechanism of the compound of the present invention, the compound can enhance the function of neural stem cells, and therefore is effective for Huntington disease and amyotrophic lateral sclerosis. According to the action mechanism of the compound of the present invention, the compound is also effective for depression and stroke. During the onset of depression or stroke, the occurrence of neuroinflammation in the brain is also involved, which in turn leads to the reduction of neural stem cells and the changes in neural function. The compound of formula (I) of the present invention can enhance the function of neural stem cells, from which it can be understood that the compound is effective for depression and stroke.

Based on the novel findings of the inventors, the present invention provides the use of the compound of formula (I) or an isomer, a solvate or a precursor thereof, or their pharmaceutically acceptable salts in the manufacture of a medicament or a medicine kit for preventing, alleviating or treating neurodegenerative diseases, depression or stroke.

The present invention also provides the use of the compound of formula (I) or an isomer, a solvate or a precursor thereof, or their pharmaceutically acceptable salts in the manufacture of a composition, a kit or a medicine kit for inhibiting neuroinflammation.

The present invention also provides the use of the compound of formula (I) or an isomer, a solvate or a precursor thereof, or their pharmaceutically acceptable salts in the manufacture of a composition, a kit or a medicine kit for promoting the production of neural stem cells.

The present invention also provides the use of the compound of formula (I) or an isomer, a solvate or a precursor thereof, or their pharmaceutically acceptable salts in the manufacture of a composition, a kit or a medicine kit for reducing the production of Aβ.

The present invention also provides the use of the compound of formula (I) or an isomer, a solvate or a precursor thereof, or their pharmaceutically acceptable salts in the manufacture of a composition, a kit or a medicine kit for increasing the number of dopaminergic neurons in substantia nigra.

The present invention also provides the use of the compound of formula (I) or an isomer, a solvate or a precursor thereof, or their pharmaceutically acceptable salts in the manufacture of a composition, a kit or a medicine kit for increasing the level of striatal dopaminergic nerve fibers.

The compound of formula (II) (PL201), the compound of formula (III) (PL202), the compound of formula (IV) (PL172) and the compound of formula (V) (PL171) provided by the present invention have excellent effects in the above-mentioned uses, wherein the compounds of formula (III) and formula (V) have particularly excellent effects.

Pharmaceutical Composition

The present invention also provides a pharmaceutical composition, which contains (a) an effective amount of the compound of formula (I), or an isomer, solvate, precursor, or their pharmaceutically acceptable salts; and (b) a pharmaceutically acceptable carrier or excipient.

In the pharmaceutical composition of the present invention, the compound of formula (I) or an isomer, a solvate or a precursor thereof, or their pharmaceutically acceptable salts is in an effective amount. For example, the compound of formula (I) or a pharmaceutically acceptable salt thereof in a weight ratio of 0.001%-50% may be contained. Preferably, the pharmaceutical composition contains the compound of formula (I) or a pharmaceutically acceptable salt thereof in a weight ratio of 0.01%-20%.

The dosage form of the pharmaceutical composition of the present invention may be various, as long as it can effectively bring the active ingredient to the mammalian body. For example, it can be selected from a powder, a pulvis, a tablet, a pill, a capsule, a sustained-release preparation, a controlled-release preparation, an injection, an infusion liquid and a suspension. According to the disease types to be treated by the compound of the present invention, a person skilled in the art can choose dosage forms that are convenient for application.

From the standpoint of ease of preparation and storage, the preferred pharmaceutical composition is solid composition, and in particular a tablet and a solid-filled or liquid-filled capsule. In terms of the particle size of ease of administration, the preferred pharmaceutical composition is an oral preparation. The compound of the present invention or the pharmaceutical composition thereof can also be stored in a sterile device suitable for injection or infusion.

The effective administration dosage of the compound of formula (I) as an active ingredient may vary depending on the route of administration and the severity of the disease to be treated. Nevertheless, generally, the compound of the present invention can obtain satisfactory results when administered at a dose of about 0.01-100 mg/kg animal weight daily, preferably administered in 1-3 divided doses daily or administered in a sustained-release form. The dose regimen can be adjusted to provide the best therapeutic response. For example, depending on the urgent need of the treatment situation, several divided doses can be administered daily, or the dose can be reduced proportionally.

The present invention is further described below in conjunction with specific examples. It is to be understood that these examples serve only to illustrate the present invention and are not limiting the scope of the present invention. In the following examples, experimental methods without specifying specific conditions are generally performed under conventional conditions, for example, those described by J. Sambrook et al., Molecular Cloning: A Laboratory Manual, the third edition, Science Press, 2002, or the conditions recommended by the manufacturer.

Statistical Analysis of Data

All experimental data are expressed as mean f standard error. T test was used for comparison between different treatment groups. One-way ANOVA was used to analyze the results between multiple groups, and post-test was performed using Fisher's protected least significant difference test or Bonferroni t test, or two-way ANOVA was used to perform analysis, and post-test was performed using Tukey post hoc test. When P<0.05, there was a significant difference between groups.

Example 1. PL201 Improves Learning and Memory of AD Mice

Morris Water Maze Test

Twenty 5-6 months aged, male APP/PS1 transgenic mice (AD mice) were selected, and were divided into a model group and a polysaccharide administration group randomly by random number table method. PL201 was intragastrically administered daily (10 mg/kg mouse body weight), meanwhile, 10 non-transgenic mice were used as a negative control group (without PL201 administration). After 90 days of consecutive administration, Morris water maze behavior test was used to detect the effects of PL201 on learning and cognitive function of APP/PS1 mice.

Classic Morris water maze test procedure was used in the test, which includes two parts: i.e., the place navigation task and the spatial probe task. The test lasted for 7 days, and the spatial probe task was added at Day 4 and Day 7.

It can be seen from the test results in FIG. 1 that the escape latency of all the three groups of animals after 3 days of training was shortened in the place navigation task, illustrating that mice in each group can successfully complete the spatial learning task of the water maze. The escape latency was used as a test indicator.

The results showed that the mice in the negative control group were rapidly in response, and can quickly find the platform after entering the water. With the increase of training times, the latency time of searching for the platform was shortened. The mice in the model group were slow in response, and they had a circle drawing behavior along the barrel wall after entering the water, but there was no escape behavior. After leading the mice to the platform manually, they jumped into water again. After many times of training, they finally found the platform, but the latency of searching for the platform was significantly prolonged. With the increase of training times, the ability of searching for platform of the mice in the administration groups was improved continuously. All mice in the above three groups had a certain spatial memory ability, wherein mice in the model group had a worse performance for escape latency than mice in the control group, suggesting that the learning and memory ability of mice in the model group was decreased, and the learning and memory disorder of AD was simulated well by mice in the model group. Compared to the model group, the latency of mice in the administration group was significantly different. It can be seen that the learning and memory abilities of AD mice after the administration of PL201 were significantly improved.

Example 2. PL201 Promotes Neurogenesis In Vivo

Abnormal neurogenesis, neuroinflammation and deposition of Aβ plaques are closely related to the decline in cognitive ability of AD. Therefore, in this example, it is further explored whether PL201 has an effect on neurogenesis.

The inventors conducted PL201 administration experiments on AD mice (5-6 months aged AD mice were selected). Each mouse was intragastrically administrated 100 μl PL201, and the dosage was 10 mg/kg mouse body weight. Moreover, mice in the control group were administrated 100 μl water once daily for 90 days, and from Day 60 were intraperitoneally injected with 5-bromo-2'-deoxyuridine (BrdU) of 50 mg/kg mouse body weight once daily for 7 days. After 90 days of administration, the mice were perfused with PFA after anesthesia, and the whole brain was taken for further experiments.

For the obtained whole brain, a mature neuron marker NeuN in the hippocampus of mice was detected: The brain of mouse which had been perfused with PFA was then fixed in 4% PFA for 24 hours, and then kept for 72 hours in 30% sucrose for cryoprotection. After the treatment was completed, the region of cerebellum was removed, and the olfactory bulb was placed upright on the filter paper and frozen at −80° C. for at least 24 hours. The frozen sectioning was performed vertically and longitudinally with a thickness of 30 μm. A total of 8×9×=72 slices (2.16 mm) including DG portion were cut and arranged in slicing order. One slice was taken from every 8 slices and combined into a group of brain slices for staining. The sliced brain slices were placed in a tissue protection solution (30% sucrose, 30% ethylene glycol, 0.1M PB), the brain slices obtained this way can be stored at −20° C. for at least half a year. During staining, a group of brain slices were taken and blocked in a blocking solution (10% donkey serum, 0.3% TritonX-100, PBS) for 45 minutes at room temperature, and then primary antibodies were added and incubated overnight at 4° C. (dilution ratio of primary antibodies were: rat anti-BrdU, 1:2000; rabbit anti-Ki67, 1:1000; goat anti-Dcx, 1:200; mouse anti-NeuN, 1:200; and goat anti-Sox2, 1:60), and then same were incubated with a suitable fluorescent secondary antibody for 1 hour at room temperature. Nuclear staining was performed with DAPI. The images of stained brain slices were then taken with Olympus FV100i or Leica SP-8. The number of single or double positive cells was analyzed by Image Pro Plus software. For antigen retrieval, the brain slices were treated in the antigen retrieval solution (10 mM sodium citrate, pH 6.5) at 95° C. for 20 minutes before serum blocking. For BrdU staining, before serum blocking, the brain slices were treated with 2 M hydrochloric acid at 37° C. for 30 minutes and then were washed with 0.1 M boric acid buffer (pH 8.5).

Figure 2:
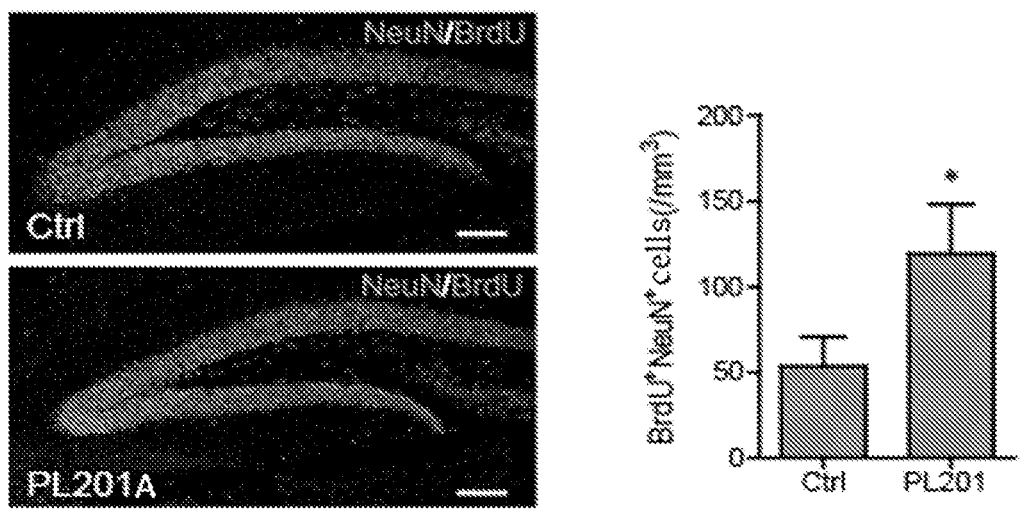
FIG. 2. PL201 promotes neurogenesis in vivo.

The inventors have found that compared to mice in the control group, the hippocampus in the mice administrated with PL201 had more BrdU/NeuN double-positive newborn neurons, see FIG. 2.

The above results indicated that PL201 can remarkably promote neurogenesis in mice.

Example 3. PL201 Alleviates the Inhibitory Effect of Aβ on Proliferation of Neural Stem Cells In Vitro As the main pathogenic protein of AD, Aβ inhibits neural stem cell proliferation. In this example, the inventors detected the levels of human neural stem cell proliferation by EdU incorporation, and tested whether PL201 can alleviate the inhibition effect of Aβ on the proliferation of neural stem cells.

Human neural stem cells (3 L) were cultured in DMEM/F12 (containing N2/B27 and 10 ng/ml bFGF), plated to 96 well plates and incubated for 24 hours, then Aβ (5 μM) was added to pre-treat the cells for 30 minutes, and then PL201 (30 μM) was added. After co-incubation for 72 hours, the proliferation level of neural stem cells was detected by EdU staining.

Figure 3:
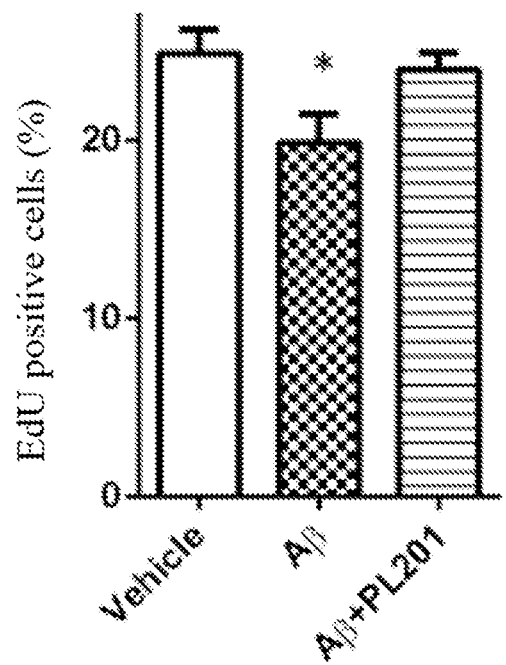
FIG. 3. PL201 alleviates the inhibition of Aβ on proliferation of neural stem cells in vitro.

The results showed that Aβ treatment inhibited neural stem cell proliferation, whereas the addition of PL201 can significantly alleviate the inhibitory effect of Aβ on the proliferation of neural stem cells, see FIG. 3.

Example 4. PL201 Inhibits Neuroinflammation

Neuroinflammation in the brain of AD is one of the causes of cognitive decline. Microglial cells are the key cells that mediate neuroinflammation. In this example, the inventors have explored whether PL201 has the effect of inhibiting neuroinflammation by detecting the expressions of inflammatory factors on mouse BV-2 cell line.

BV-2 cells were cultured in DMEM, plated to 24 well plates and cultured for 24 hours, then PL201 (0, 10, 30, and 100 μM) and LPS (300 ng/ml) were added. After co-incubation for 24 hours, Trizol was used to extract RNA and the expressions of related inflammatory factors were detected by QPCR.

Figure 4:
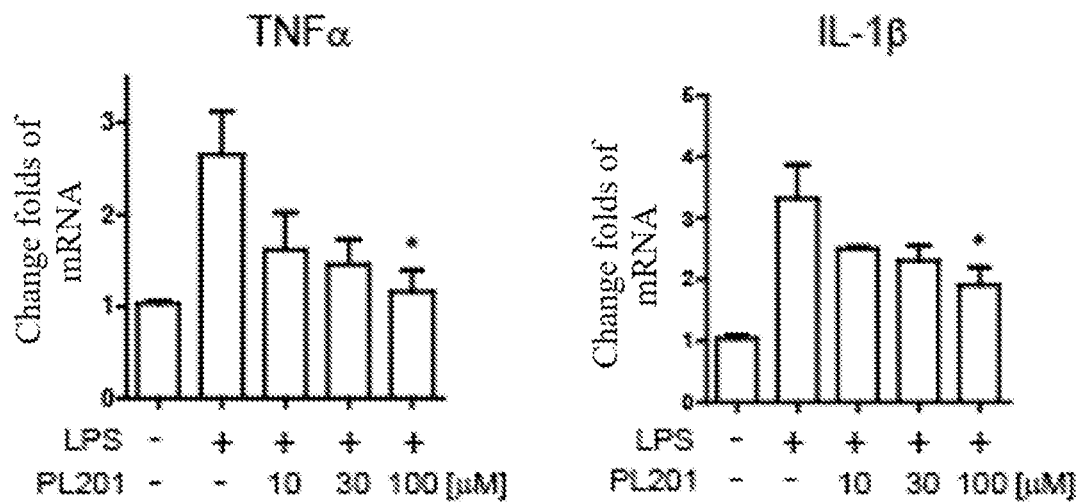
FIG. 4. PL201 inhibits neuroinflammation.

The results showed that PL201 treatment can significantly inhibit the expressions of inflammatory factors TNFα and IL-1β, and even had an obvious effect at a lower dosage, see FIG. 4.

Example 5. PL201 Decreases the Number of Aβ Plaques In Vivo

The deposition of Aβ plaques in AD brain is one of the key causes of nerve injury, which would in turn cause the decline of cognitive ability. Therefore, in this embodiment, it is further explored whether PL201 has an effect on the number of Aβ plaques in the brain.

The inventors performed frozen sectioning coronally with a thickness of 30 μm on the whole brain sample of AD mice after administration in example 2, and the slices were stained with thioflavin S and DAPI. The stained brain slices were then photographed with Olympus FV100i or Leica SP-8.

Figure 5:
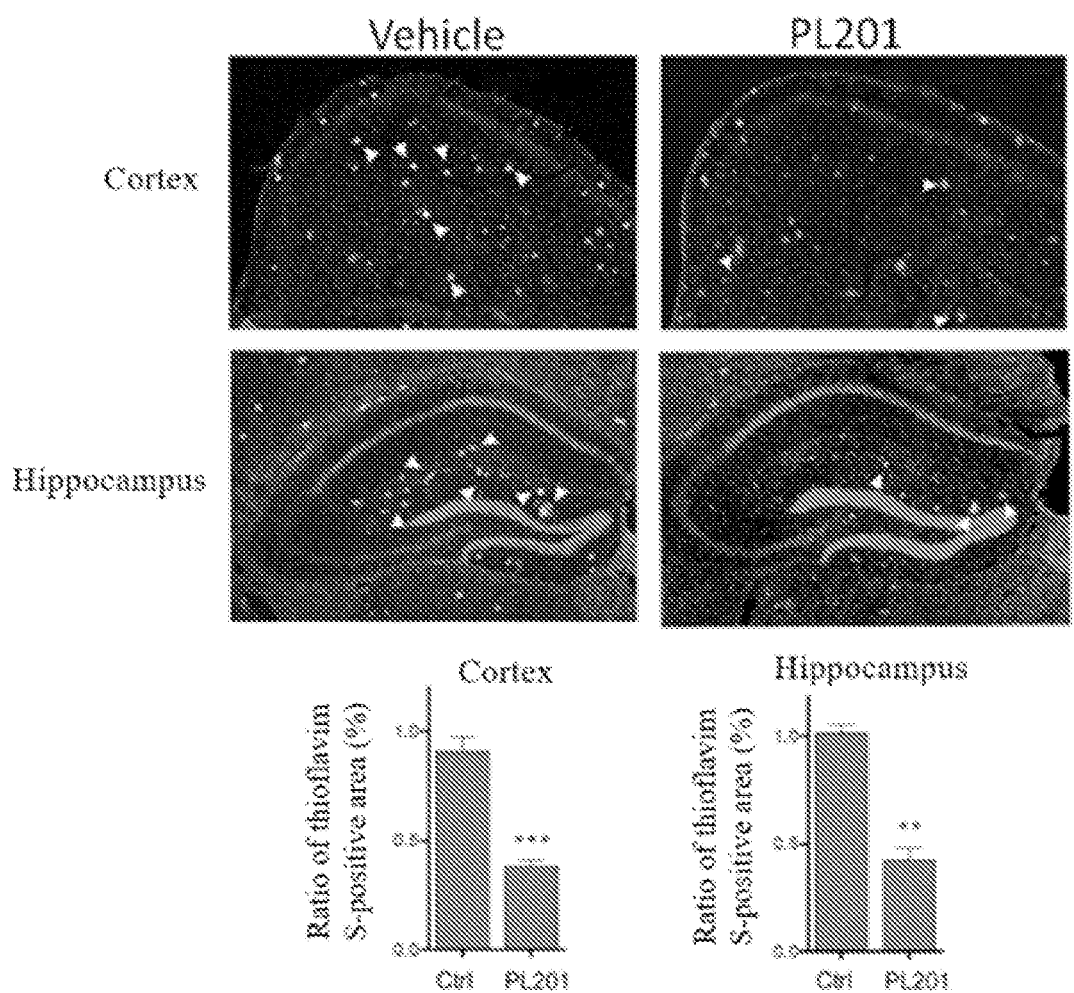
FIG. 5. PL201 decreases the number of Aβ plaques in vivo.

The inventors have found that compared to the control group, the brains of mice administrated with PL201 had less Aβ plaques, see FIG. 5.

The above results indicated that PL201 significantly reduced the Aβ plaques in mice.

Example 6. PL201 Reduces Aβ Production

As is the main pathogenic protein of AD. In this example, the inventors have explored whether PL201 has the effect of reducing Aβ production by detecting the level of Aβ on neuroblastoma cells SK-N-SH.

Culture of neuroblastoma cells SK-N-SH and Aβ detection: SK-N-SH cells were cultured in DMEM, plated to 24 well plates and cultured for 24 hours, then PL201 (0, 30, 100, and 300 μM) was added. After co-incubation for 24 hours, the protein level of total Aβ in supernatant was detected by ELISA.

Figure 6:
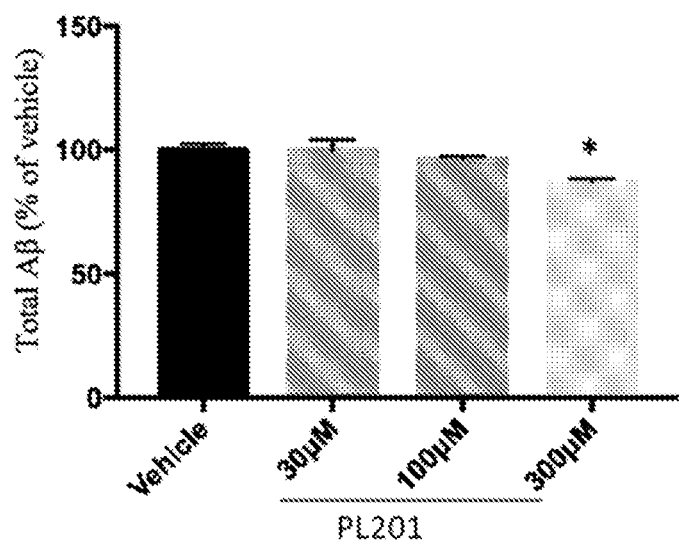
FIG. 6. PL201 reduces Aβ production in vitro.

The results showed that PL201 treatment significantly inhibited Aβ production, see FIG. 6.

Example 7. PL201 Increases Mitochondrial Membrane Potential

Mitochondrial membrane potential is the main parameter of mitochondrial function, and mitochondrial dysfunction is a prominent feature of AD brain. In this example, the inventors have explored whether PL201 has the effect of improving mitochondrial function by detecting the level of cell mitochondrial membrane potential of human neural stem cells.

Mitochondria was stained with JC-1 for 20 minutes and washed with washing buffer, then immunofluorescence analysis was performed.

Figure 7:
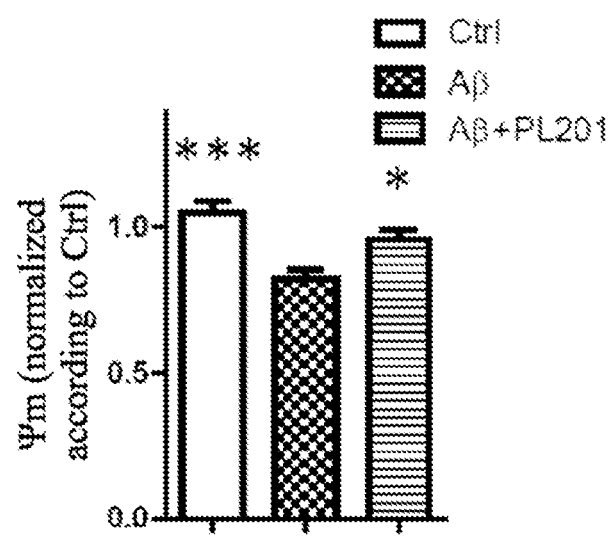
FIG. 7. PL201 increases mitochondrial membrane potential.

The results showed that Aβ treatment reduced mitochondrial membrane potential, whereas PL201 treatment mitigated the deleterious effect of Aβ to a lesser extent, see FIG. 7.

Example 8. PL201 Improves AMPK Phosphorylation Level

The changes of mitochondrial function are closely related to the regulation of metabolism signaling including AMPK, which is also widely considered to be closely related to the pathogenesis of AD. In this example, the inventors have explored whether PL201 has an effect on metabolism signaling by detecting the level of AMPK phosphorylation in human neural stem cells via western blot.

Human neural stem cells (3 L) were cultured in DMEM/F12 (containing N2/B27 and 10 ng/ml bFGF), plated to 12 well plates and cultured for 24 hours, then Aβ (5 μM) was added to pre-treat the cells for 30 minutes, and then PL201 (30 PM) was added. After co-incubation for 72 hours, the cells were washed with PBS and lysed with Laemmli's sample buffer, then SDS PAGE electrophoresis was performed to detect associated protein bands with rabbit anti-phospo-AMPK and total AMPK antibody.

Figure 8:
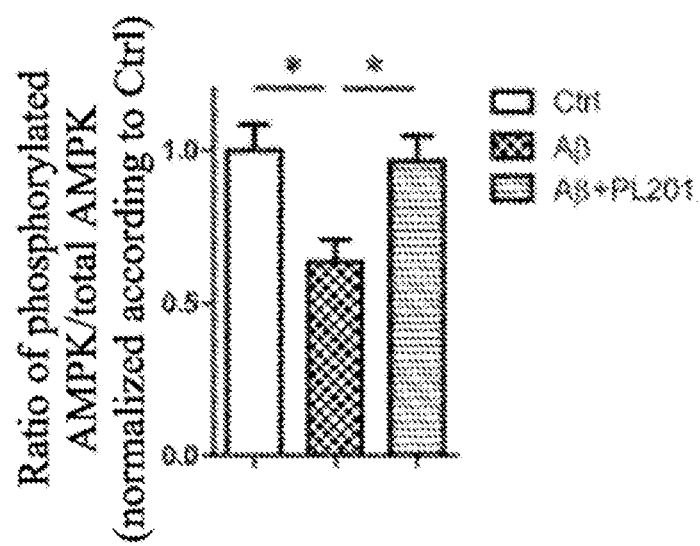
FIG. 8. PL201 improves AMPK phosphorylation level.

The results showed that Aβ treatment reduced AMPK phosphorylation level, whereas PL201 treatment reduced the extent of this decline, see FIG. 8.

Example 9. PL201 Improves the Performance of Mice in Pole-Climbing Test

MPTP has a selectively destructive effect on dopaminergic neurons in brain substantia nigra. MPTP-induced Parkinsonism is the most classic animal model which reproduce most of the clinical and pathological hallmarks of Parkinson's disease. PD mainly manifests as symptoms such as resting tremor, hypertonia and hypomotor. The time to turn around and the time to climb down in pole-climbing test can represent the overall motor coordination ability of mice.

The mice were randomly divided into 4 groups: a group in which the mice was administrated with normal saline (NS), a MPTP model group in which the mice was intragastrical administrated with normal saline (NS 4 MPTP), a group in which the mice was intragastrical administrated with 50 mg of compound PL201 (PL201), and a MPTP model group in which the mice was intragastrical administrated with compound PL201 (PL201+MPTP).

11 animals were set in the group in which the mice was administrated with normal saline (NS), 14 animals were set in the MPTP model group in which the mice was intragastrical administrated with normal saline (NS+MPTP), 4 animals were set in the group in which the mice was intragastrically administrated with 50 mg of compound PL201 (PL201), 15 animals were set in the MPTP model group in which the mice was intragastrically administrated with the compound PL201 (PL201+MPTP).

The administration started on the day of animal grouping: mice in the NS and the NS+MPTP group were intragastrically administrated with normal saline, and mice in the other two groups were administrated with compound PL201 once a day for 7 consecutive days. From Day 7, mice in the NS and the PL201 group were intraperitoneally injected with 5 ml/kg normal saline, while mice in the NS+MPTP and the PL201+MPTP group were intraperitoneally injected with 25 mg/kg of MPTP once a day for a total of 5 days.

On Day 3 of the experiment, the pole-climbing test of mice was carried out to evaluate the motor coordination ability of the mice. The mouse was placed head upwards gently on the top of the rough-surfaced pole (1 cm in diameter and 50 cm in height). The time taken by the mice to turn from head upwards to head downwards completely was recorded as the time to turn around, and the time taken by the mice from moving downwards to all limbs reaching the bottom of the pole was recorded as the time to climb down. Time exceeded 30 seconds was recorded as 30 seconds. Each mouse was tested 5 times, and the average value was taken.

The results showed that on day 3 of the experiment, the mice in the NS+MPTP group spent more time to turn around and climb down longer than those in the normal saline group (NS). And administration of PL201 reduced the time to turn around and time to climb down in the PL201+MPTP group compared with the NS 4 MPTP group.

Figure 9:
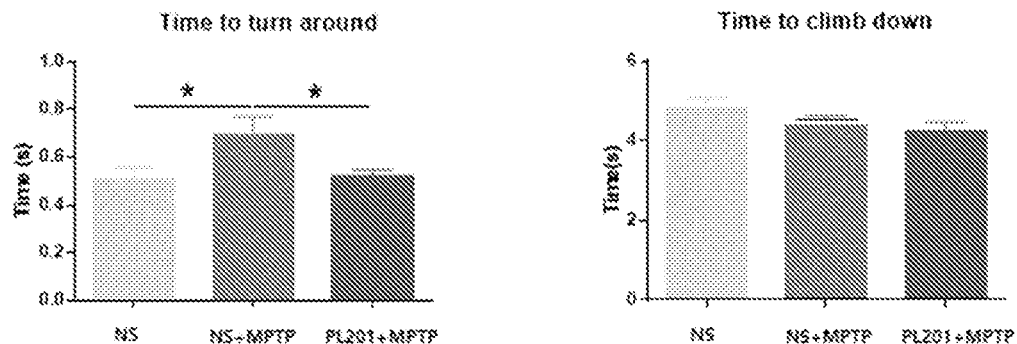
FIG. 9. PL201 improves the performance of mice in pole-climbing test.

The results showed that compound PL201 has a beneficial effect on the movement initiation and coordination ability of MPTP mice model, see FIG. 9.

Example 10. PL201 Increases the Level of Striatal Dopaminergic Nerve Fibers

The loss of dopaminergic neurons in substantia nigra and striatal dopaminergic nerve fibers is the main pathological feature of Parkinson's disease. Western blot can be used to detect the loss of striatal dopaminergic nerve fibers to explore the effect of PL201 on the level of striatal dopaminergic nerve fibers.

The mice were randomly divided into 4 groups: a group in which the mice was administrated with normal saline (NS), a MPTP model group in which the mice was intragastrical administrated with normal saline (NS+MPTP), a group in which the mice was intragastrical administrated with 50 mg of compound PL201 (PL201), and a MPTP model group in which the mice was intragastrical administrated with compound PL201 (PL201+MPTP).

11 animals were set in the group in which the mice was administrated with normal saline (NS), 14 animals were set in the MPTP model group in which the mice was intragastrical administrated with normal saline (NS+MPTP), 4 animals were set in the group in which the mice was intragastrically administrated with 50 mg of compound PL201 (PL201), 15 animals were set in the MPTP model group in which the mice was intragastrically administrated with the compound PL201 (PL201+MPTP).

The administration started on the day of animal grouping: mice in the NS and the NS+MPTP group were administrated with normal saline, and mice in the other two groups were administrated with compound PL201 once a day for 7 consecutive days. From Day 7, mice in the NS and the PL201 group were intraperitoneally injected with 5 ml/kg normal saline, while mice in the NS+MPTP and the PL201+MPTP group were intraperitoneally injected with 25 mg/kg of MPTP once a day for a total of 5 days.

On Day 7 after MPTP modeling, animals in each group were anesthetized with 10% chloral hydrate. After perfusion, the striatum was isolated from the brain tissue and placed in 1.5 ml EP tubes, and 250 μl RIPA lysis buffer (Thermo Fisher) was added to perform ultrasonic disruption of the tissue, and the supernatant was collected to detect the protein concentration. The protein concentration was adjusted to 2 μg/l and 5× loading buffer (reducing) was added, boiling was performed to denature protein. The sample was added to 10% SDS-polyacrylamide gel electrophoresis, and was transferred to a methanol-activated PVDF membrane at 100 V. TBST containing 5% skimmed milk was used for blocking at room temperature for 1 h, and the primary antibody of TH (1:1000) was added and incubated overnight at 4° C. Non-specifically binding of primary antibody was washed off with TBST buffer, and then goat anti-mouse/rabbit fluorescent secondary antibody (LI-COR) was added. After incubation at room temperature for 1 h, washed with TBST buffer for 3 times. The fluorescence signal was detected by Odyssey near-infrared fluorescence scanner and made statistics.

Figure 10:
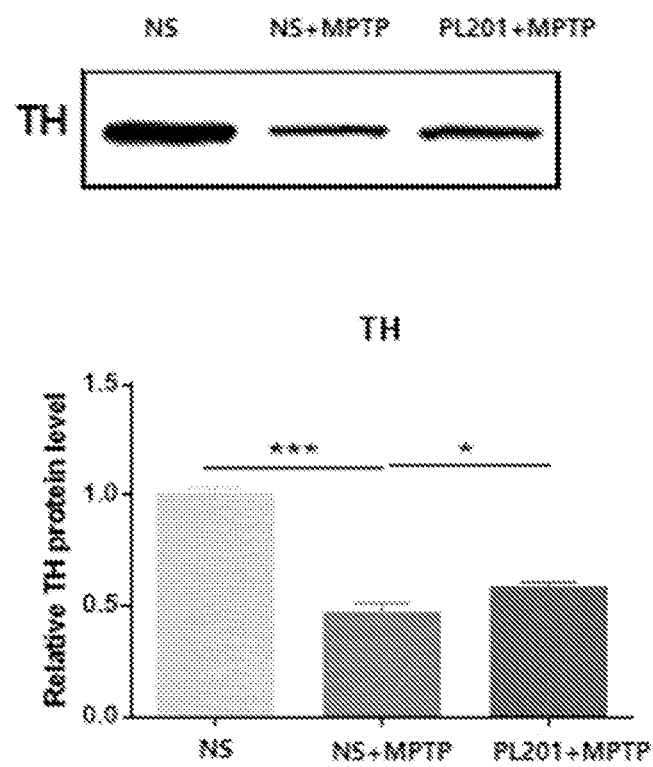
FIG. 10. PL201 increases the level of striatal dopaminergic nerve fibers.

The results showed that compared with the NS+MPTP group, the level of striatal dopaminergic nerve fibers was significantly increased in PL201+MPTP group after 7 days of MPTP modeling. Compound PL201 increased the level of striatal dopaminergic nerve fibers in mice, suggesting it could protect the striatal dopaminergic nerve fibers from MPTP-induced injury, see FIG. 10. The results showed that compound PL201 ameliorated the pathogenesis of Parkinson's disease.

Example 11. PL201 Increases the Number of Dopaminergic Neurons in Substantia Nigra and the Level of Striatal Dopaminergic Nerve Fibers The loss of dopaminergic neurons in substantia nigra and striatal dopaminergic nerve fibers is the main pathological feature of Parkinson's disease. Tyrosine hydroxylase (TH) immunohistochemistry can be used to detect the loss of striatal dopaminergic nerve fibers to explore whether PL201 has the effect of increasing the number of dopaminergic neurons in substantia nigra.

The mice were randomly divided into 4 groups: a group in which the mice was administrated with normal saline (NS), a MPTP model group in which the mice was intragastrical administrated with normal saline (NS+MPTP), a group in which the mice was intragastrical administrated with 50 mg of compound PL201 (PL201), and a MPTP model group in which the mice was intragastrical administrated with compound PL201 (PL201+MPTP).

11 animals were set in the group in which the mice was administrated with normal saline (NS), 14 animals were set in the MPTP model group in which the mice was intragastrical administrated with normal saline (NS+MPTP), 4 animals were set in the group in which the mice was intragastrically administrated with 50 mg of compound PL201 (PL201), 15 animals were set in the MPTP model group in which the mice was intragastrically administrated with the compound PL201 (PL201+MPTP).

The administration started on the day of animal grouping: mice in the NS and the NS+MPTP group were intragastrically administrated with normal saline, and mice in the other two groups were administrated with compound PL201 once a day for 7 consecutive days. From Day 7, mice in the NS and the PL201 group were intraperitoneally injected with 5 ml/kg normal saline, while mice in the NS+MPTP and the PL201+MPTP group were intraperitoneally injected with 25 mg/kg of MPTP once a day for a total of 5 days.

On Day 7 after MPTP modeling, animals in each group were anesthetized with 10% chloral hydrate. After perfusion with 4% paraformaldehyde, the brain was taken. After being fixed for 24 hours with 4% paraformaldehyde, the samples were transferred into a 30% sucrose solution until being dehydrated (sink to the bottom). The coronary slices of midbrain and striatum were made in a freezing microtome at −20° C. The thickness of mouse brain slices was 30 microns. The primary antibody was monoclonal mouse anti-TH (1:1000, rabbit anti-mouse antibody). The primary antibody was used for incubating at room temperature for 2.5 hours and washed with TBST solution (8 g of sodium chloride, 0.2 g of potassium chloride and 3 g of Tris-base, adjust the volume to 1 L with distilled water, adjusted to pH 7.4 with hydrochloric acid) three times, and then the secondary antibody (goat anti-rabbit antibody) labeled with horseradish peroxidase (HPR) was used for incubating at room temperature for 1 hour.

Diaminobenzidine (DAB) was used for visualizing HRP signals, ethanol was used for gradient dehydration, xylene was used for tissue optical clearing and neutral gum was used for mounting. Image-pro plus software was used to analyze the stained slices. The total density of TH positive cells in substantia nigra was regarded as the dopaminergic neurons in substantia nigra, and the mean optical density of TH positive staining in striatum was used as a measure of the density of striatal dopaminergic nerve fibers.

Figure 18:
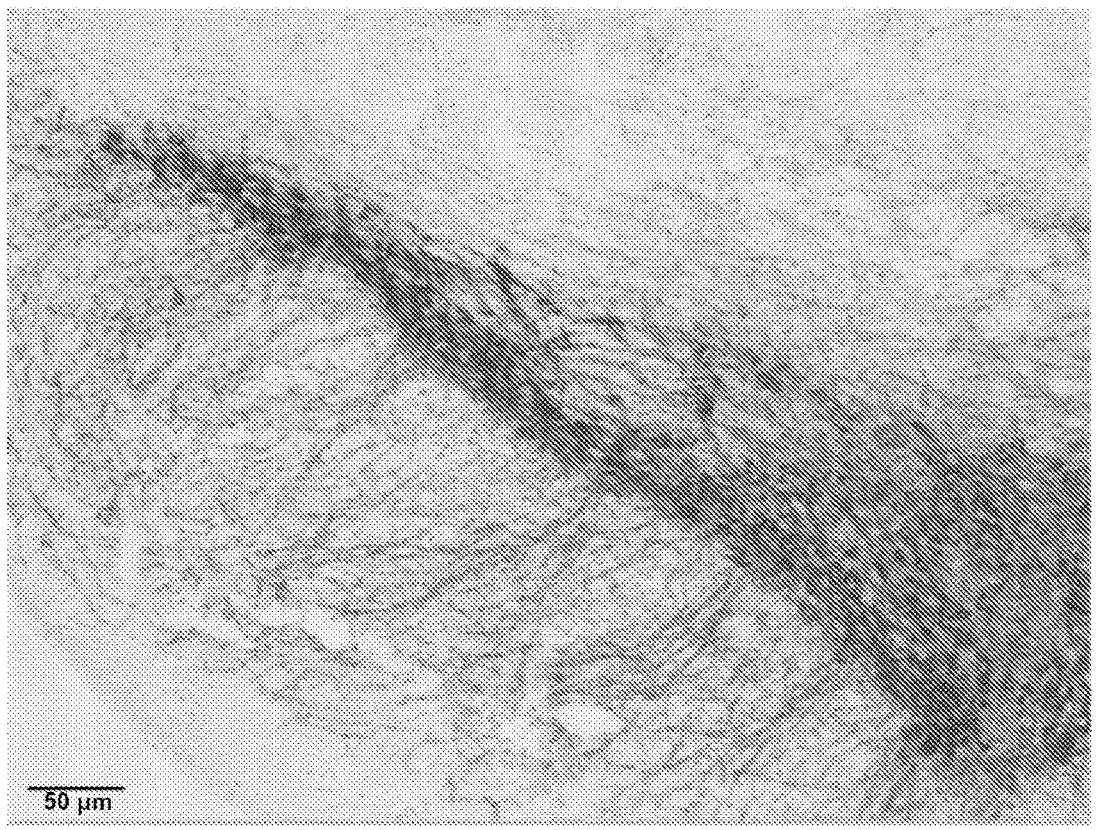
FIG. 18 is the TH staining diagram of substantia nigra, wherein figure (a) is for 1120+NS, figure (b) is for PL201+NS, figure (c) is for H₂O+MPTP, and figure (d) is for PL201+MPTP.
Figure 18:
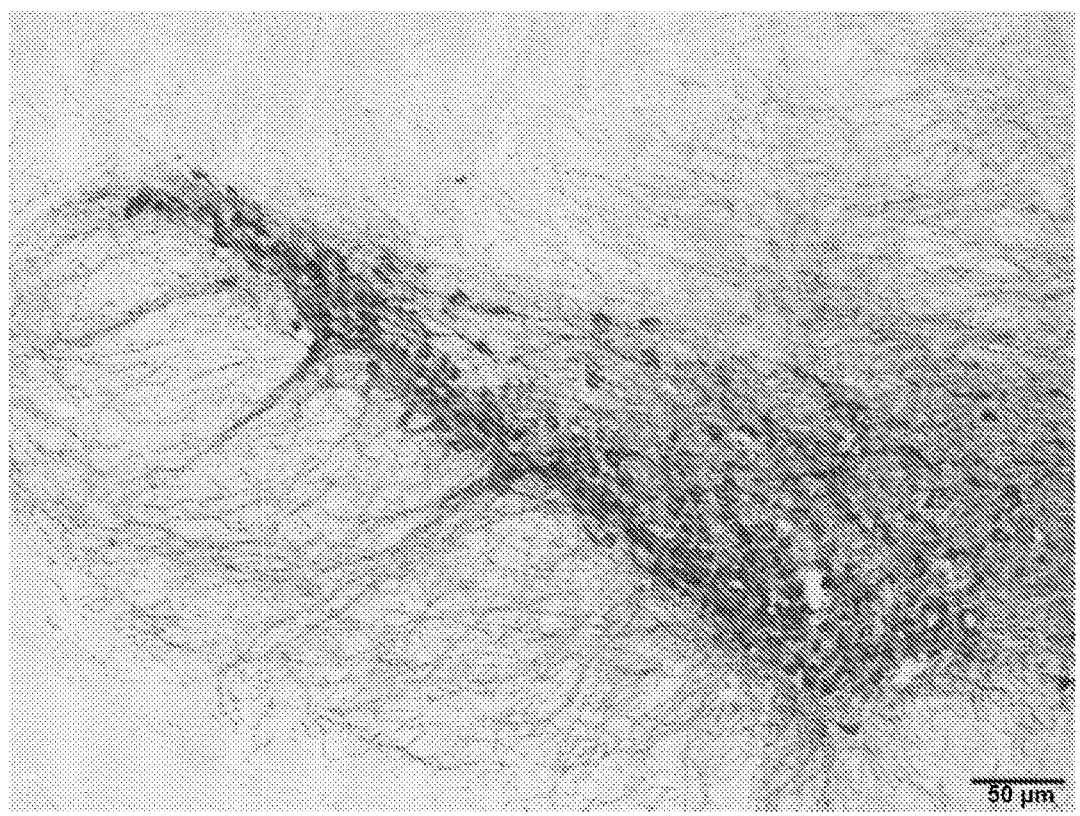
Figure 18:
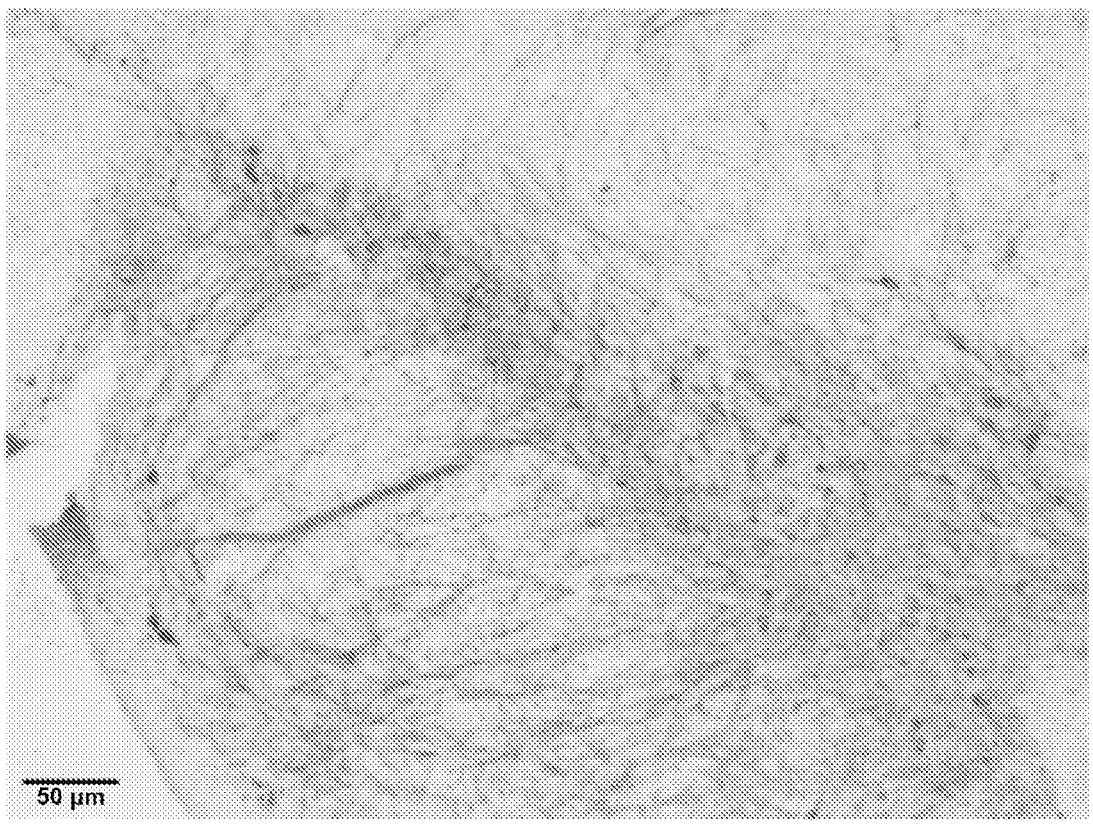
Figure 18:
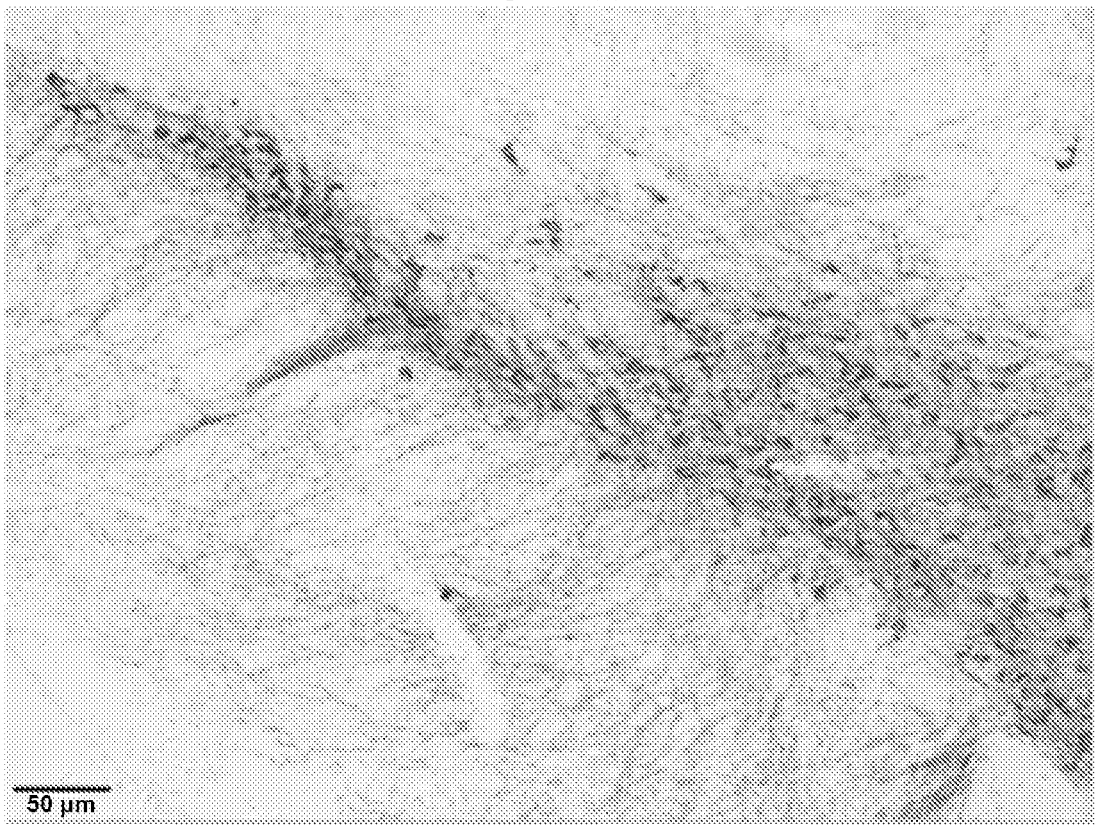

The results showed that compared with the NS+MPTP group, the number of dopaminergic neurons in substantia nigra and the level of striatal dopaminergic nerve fibers were significantly increased in PL20+MPTP group. Compound PL201 increased the level of dopaminergic neurons in substantia nigra and striatal dopaminergic nerve fibers of mice, suggesting it could protect the dopaminergic neurons in substantia nigra and striatal dopaminergic nerve fibers. The results showed that compound PL201 ameliorated the pathogenesis of Parkinson's disease, see FIG. 18.

Example 12. PL202 Reduces Aβ Production

Aβ is the main pathogenic protein of AD. In this example, the inventors have explored whether the isomer PL202 of PL201 has the effect of inhibiting and reducing Aβ production by detecting the level of Aβ on neuroblastoma cells SK-N-SH.

Figure 11:
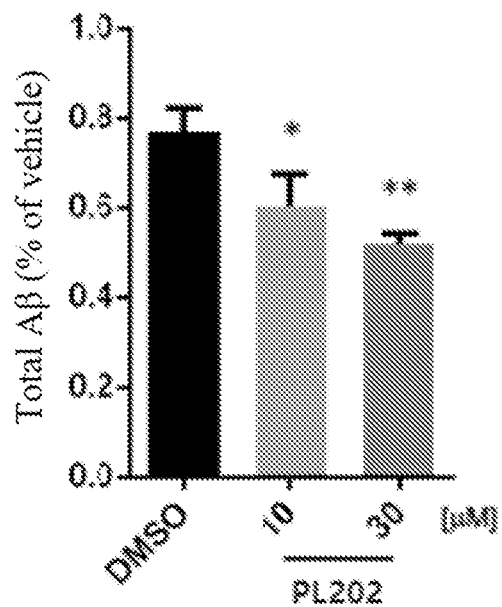
FIG. 11. PL202 reduces Aβ production.

Culture of neuroblastoma cells SK-N-SH and Aβ detection: SK-N-SH cells were cultured in DMEM, plated to 24 well plates and cultured for 24 hours, then PL202 (0, 30, and 100 μM) was added. After co-incubation for 24 hours, protein level of total Aβ in supernatant was detected by ELISA. The results showed that PL202 treatment significantly inhibited Aβ production, see FIG. 11.

Example 13. PL202 Inhibits Neuroinflammation

Neuroinflammation in the brain of AD is one of the causes of cognitive decline. Microglial cells are the key cells that mediate neuroinflammation. In this example, the inventors have explored whether PL202 has the effect of inhibiting neuroinflammation by detecting the expressions of inflammatory factors on mouse BV-2 cells.

Mouse BV-2 cells were cultured in DMEM, plated to 24 well plates and cultured for 24 hours, then PL202 (0, 30, 100, and 300 μM) and LPS (300 ng/ml) were added. After co-incubation for 24 hours, Trizol was used to extract RNA and the expressions of related inflammatory factors were detected by QPCR.

Figure 12:
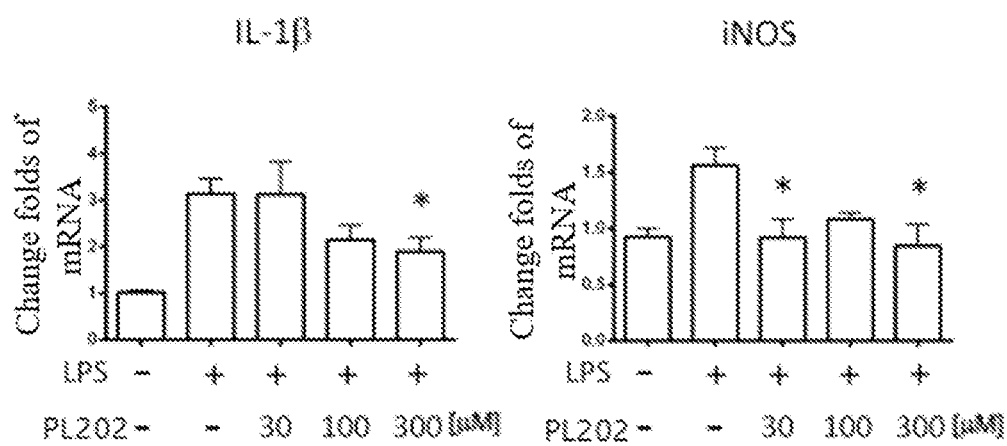
FIG. 12. PL202 reduces the expression of inflammatory factors IL-1β and iNOS.

The results showed that PL202 treatment significantly inhibited the expressions of inflammatory factors IL-1β and iNOS, see FIG. 12.

Example 14. PL171 Reduces Aβ Production

Aβ is the main pathogenic protein of AD. In this example, the inventors have explored whether PL171 has the effect of inhibiting and reducing Aβ production by detecting the level of Aβ on neuroblastoma cells SK-N-SH.

Culture of neuroblastoma cells SK-N-SH and Aβ detection: SK-N-SH cells were cultured in DMEM, plated to 24 well plates and cultured for 24 hours, then PL171 (300 μM) was added. After co-incubation for 24 hours, protein level of total Aβ in supernatant was detected by ELISA.

Figure 13:
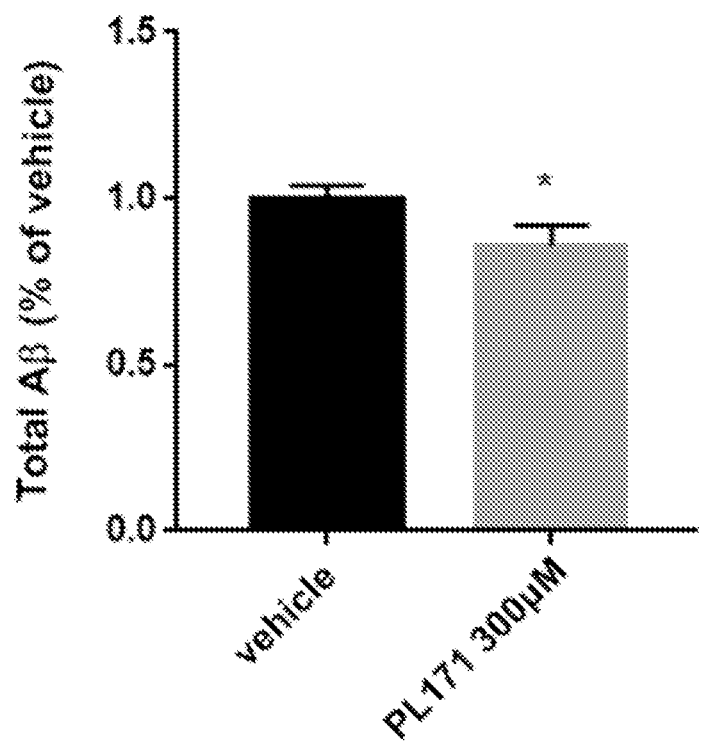
FIG. 13. PL171 reduces Aβ production.

The results showed that PL171 treatment significantly inhibited Aβ production, see FIG. 13.

Example 15. PL172 Reduces Aβ Production

Aβ is the main pathogenic protein of AD. In this example, the inventors have explored whether the isomer PL172 of PL171 has the effect of inhibiting and reducing Aβ production by detecting the level of Aβ on neuroblastoma cells SK-N-SH.

Culture of neuroblastoma cells SK-N-SH and Aβ detection: SK-N-SH cells were cultured in DMEM, plated to 24 well plates and cultured for 24 hours, then PL172 (300 μM) was added. After co-incubation for 24 hours, protein level of total Aβ in supernatant was detected by ELISA.

Figure 14:
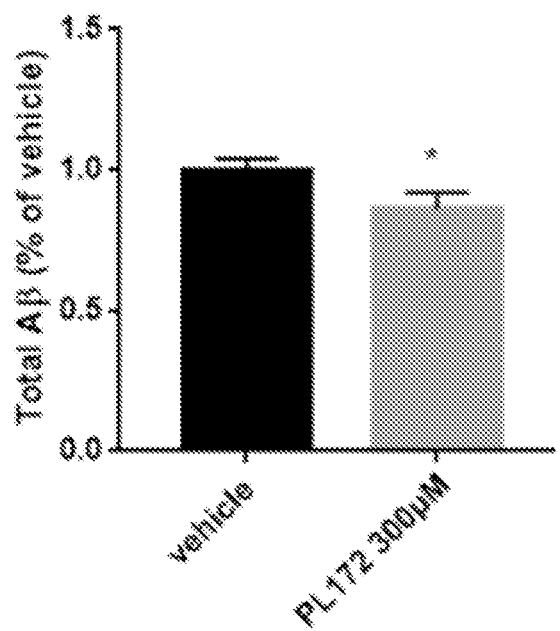
FIG. 14. PL172 reduces Aβ production.

The results showed that PL172 treatment significantly inhibited Aβ production, see FIG. 14.

Example 16. Synthesis of PL202

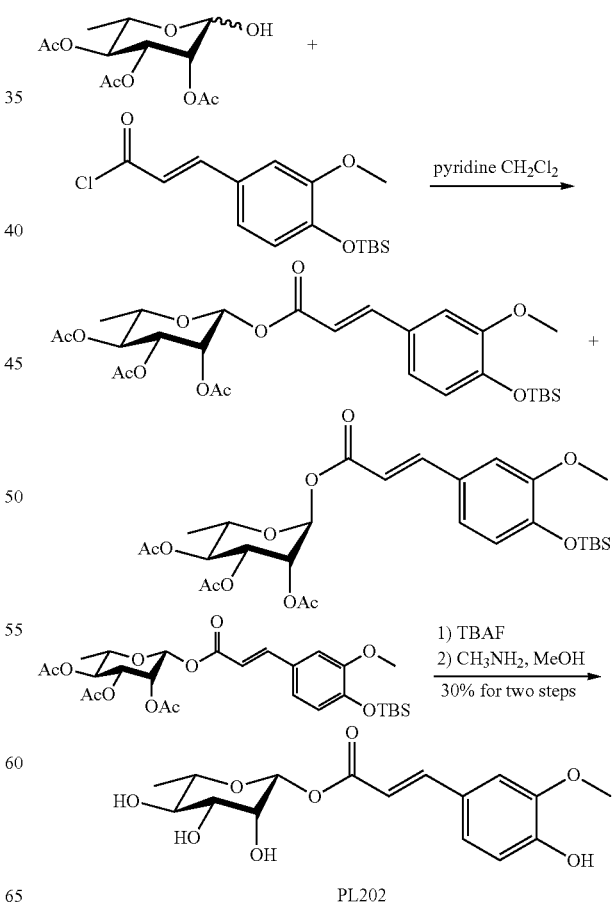

2,3,4-O-triacetyl rhamnose (5.8 g, 20 mmol) was dissolved in 100 mL anhydrous dichloromethane, and (4-O-TBS)-ferulic acid acyl chloride (6.52 g, 20 mmol) (Free Radical Res. 2015, 102) in 50 mL anhydrous dichloromethane solution and 1.0 mL of anhydrous pyridine were added dropwise under an ice bath. The reaction was stopped after stirring for 2 hours at room temperature. 200 mL of dichloromethane was added for dilution, then washed with saturated sodium chloride and dried over MgSO$_4$ and concentrated. The α glycosylation product (9.12 g, 79%) and β glycosylation product (1.1 g, 9%) were obtained respectively by column chromatography (petroleum ether: ethyl acetate=3:1). The β glycosylation product (490 mg, 0.85 mmol) was dissolved in dried THF (8.0 mL), the reaction was carried out under the action of TBAF, diluted, washed with saturated sodium chloride, dried over MgSO$_4$ and concentrated to obtain 275 mg of TBS-deprotected product. 270 mg (0.58 mmol) of the resulting product was dissolved in 3.0 mL of methanol, 0.5 mL of 33% CH$_3$NH$_2$ in methanol solution was added dropwise at 0° C., and reacted for 1 hour at 0° C. 59 mg (0.17 mmol) of PL202 was obtained by rapid concentration under reduced pressure and by column chromatography separation (ethyl acetate:methanol=6:1). ESI (+)-MS: 341.3 [M+1]$^+$; $^1$H-NMR (CD$_3$OD, 400 MHz) δ 7.80 (d, J=12 Hz, 1H), 7.23 (d, J=1 Hz, 1H), 7.12 (dd, J$_1$=8 Hz, J$_2$=1 Hz, 1H), 6.84 (d, J=6 Hz, 1H), 6.42 (d, J=13 Hz, 1H), 5.75 (d, J=1 Hz, 1H), 3.99 (d, J=2 Hz, 1H), 3.92 (s, 3H), 3.55-3.53 (m, 1H), 3.41-3.37 (m, 2H), 1.34 (d, J=4 Hz, 3H).

Figure 15A:
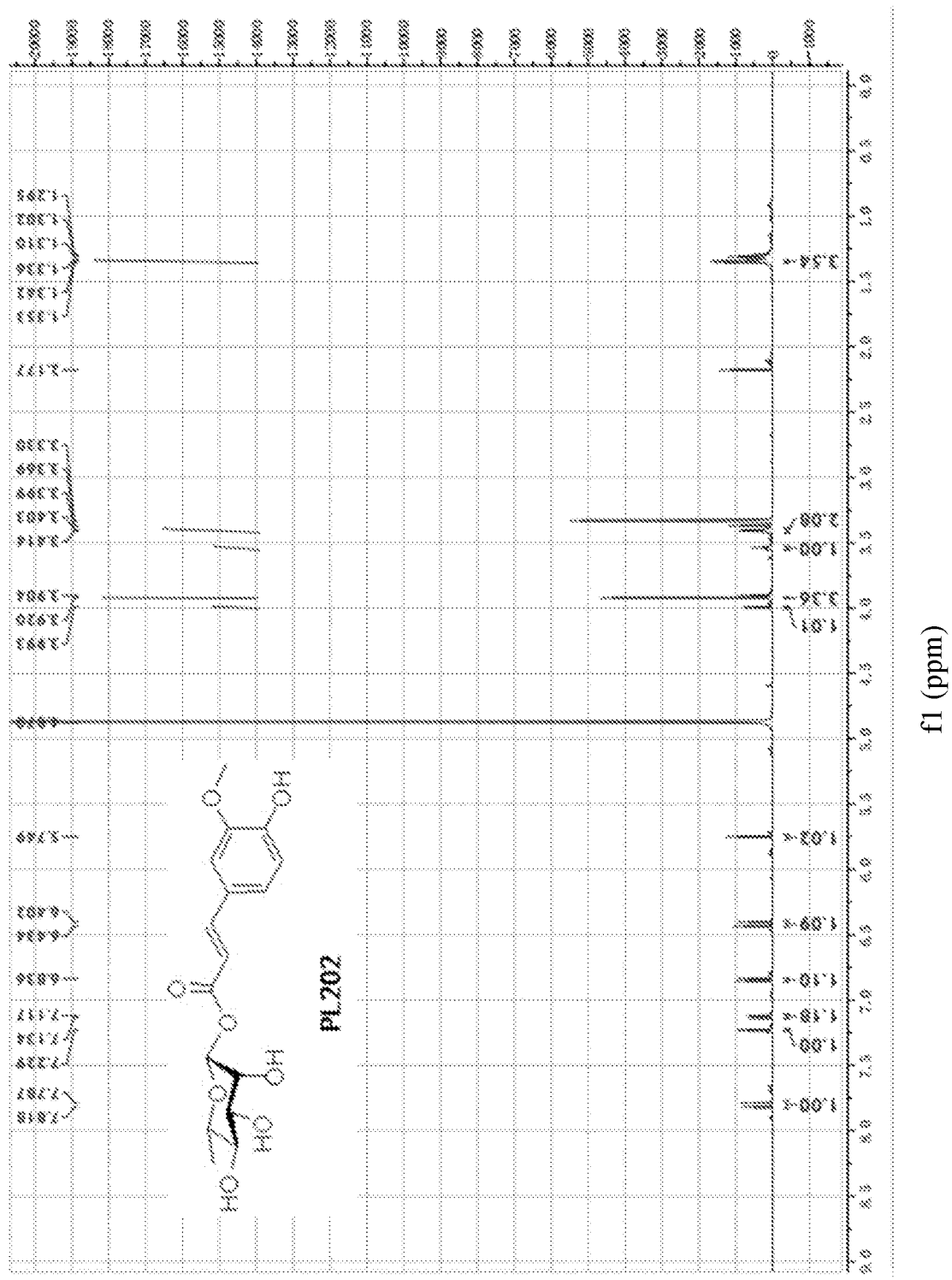
FIG. 15 is the nuclear magnetic resonance spectrum and 1D NOE spectrum of PL202, wherein figure (a) is the nuclear magnetic resonance spectrum and figure (b) is the 1 D NOE spectrum.
Figure 15B:
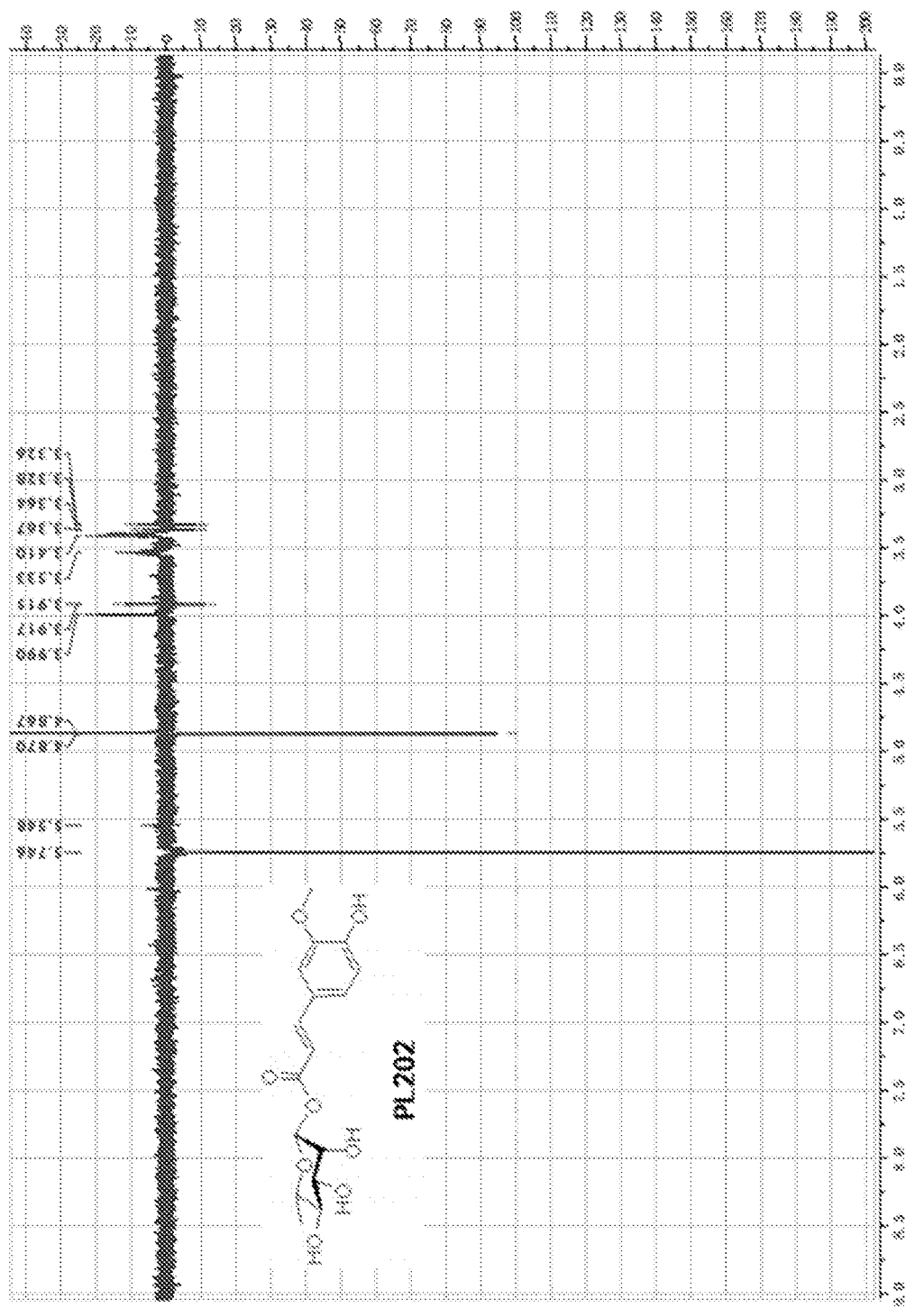
Figure 16A:
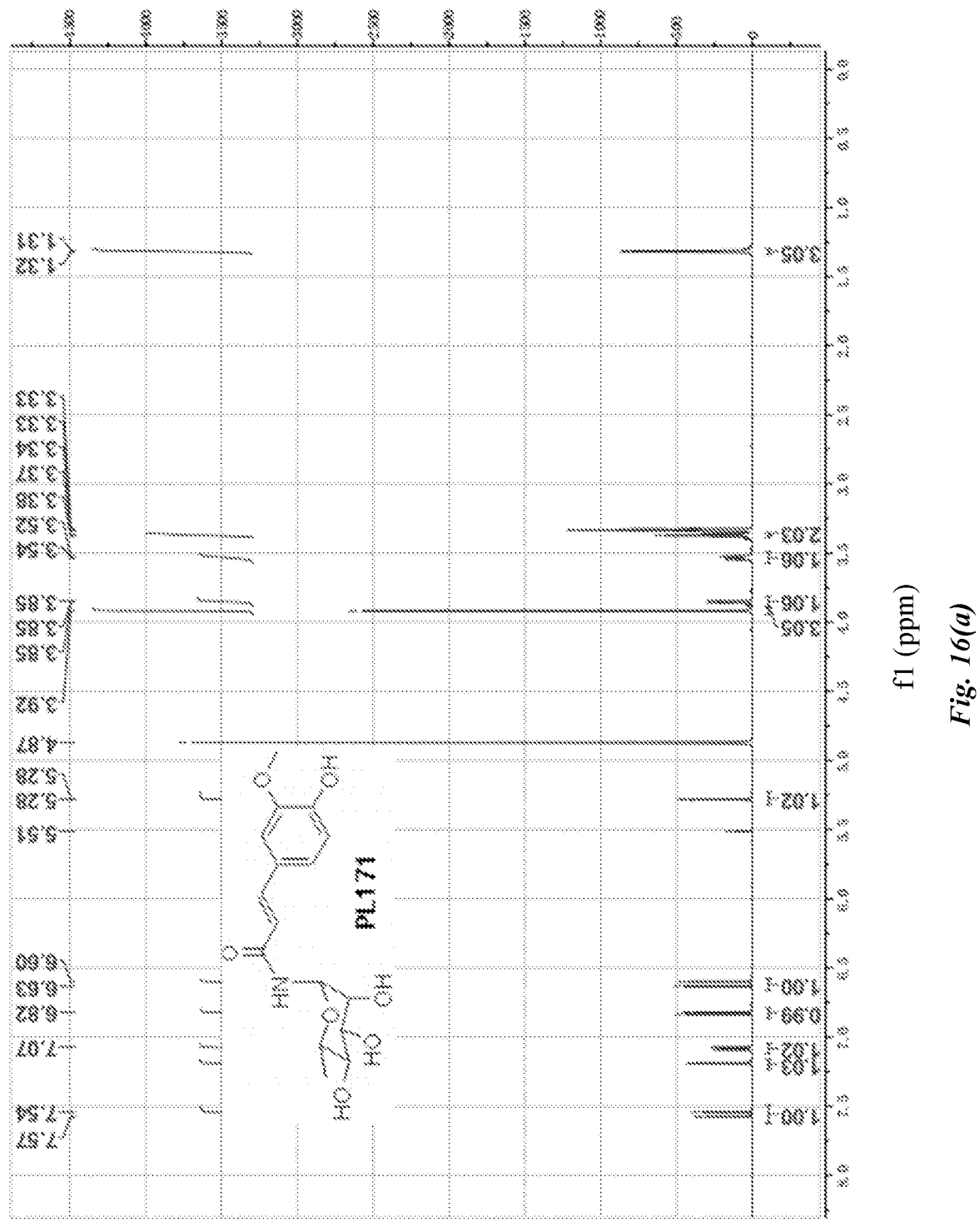
FIG. 16 is the nuclear magnetic resonance spectrum, 1D NOE spectrum and 1H-1H COSY spectrum of PL171, wherein figure (a) is the nuclear magnetic resonance spectrum, figures (b) and (c) are the 1D NOE spectrums and figure (d) is the 1H-1H COSY spectrum.
Figure 16B:
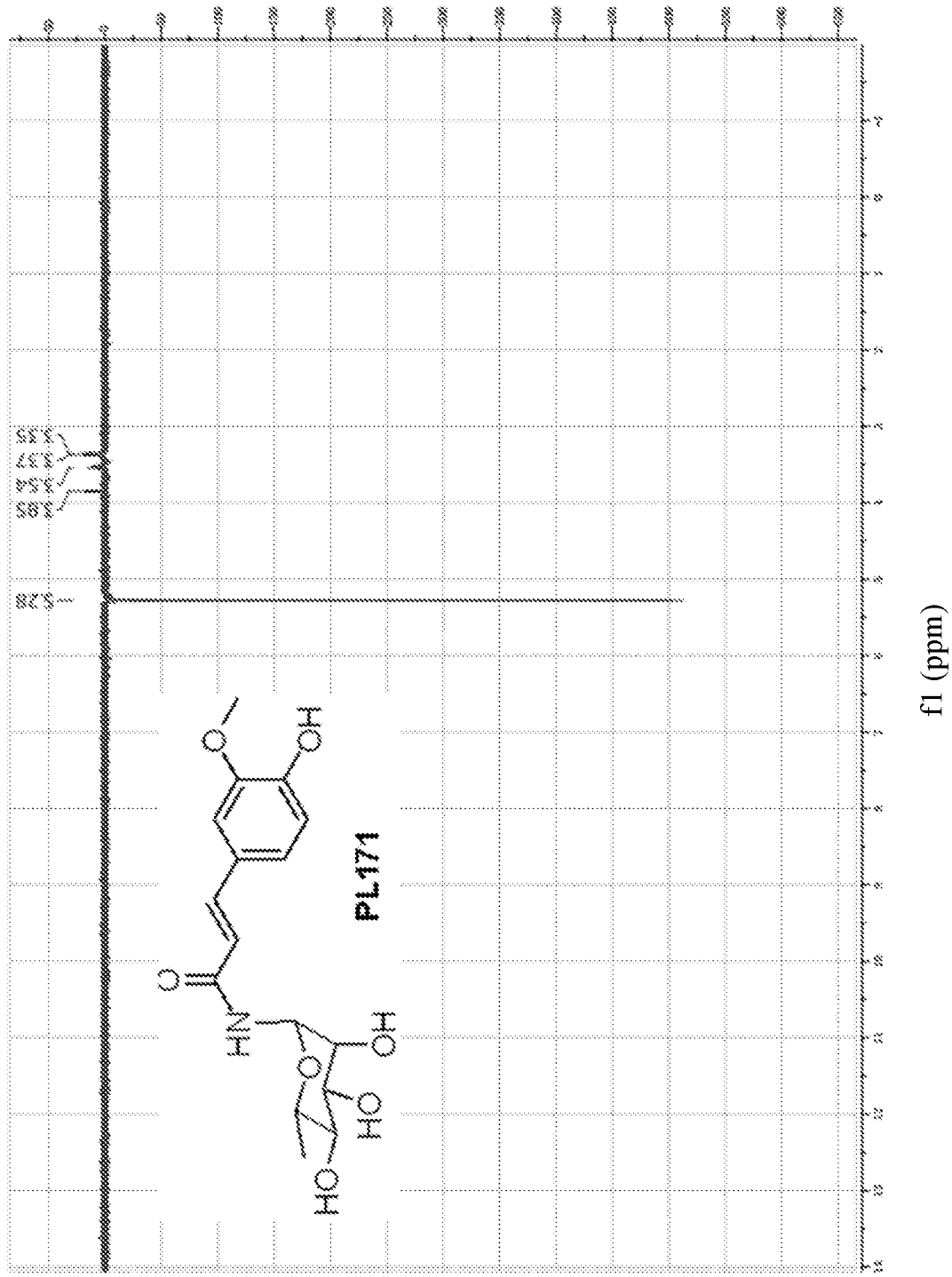
Figure 16C:
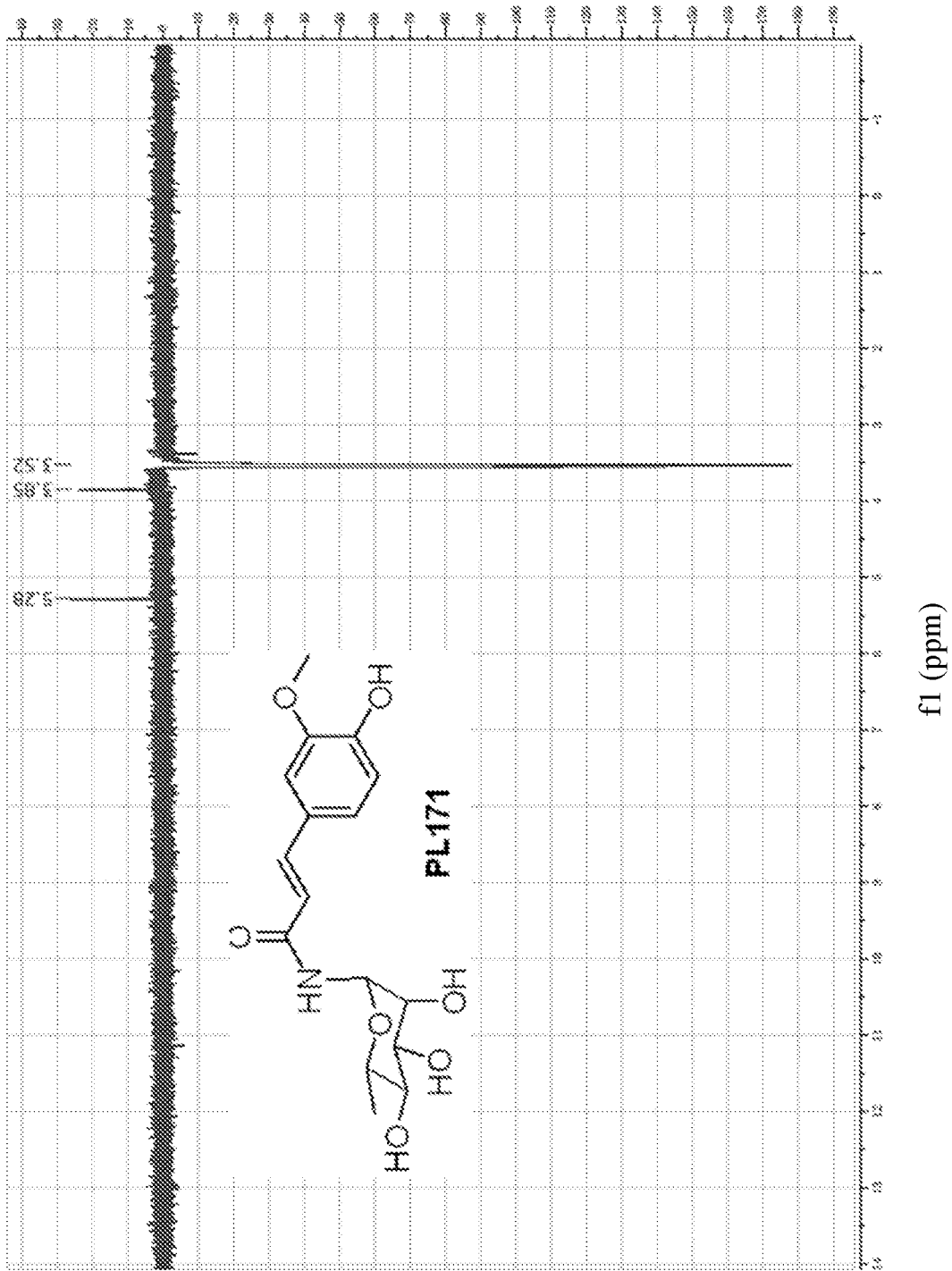
Figure 16D:
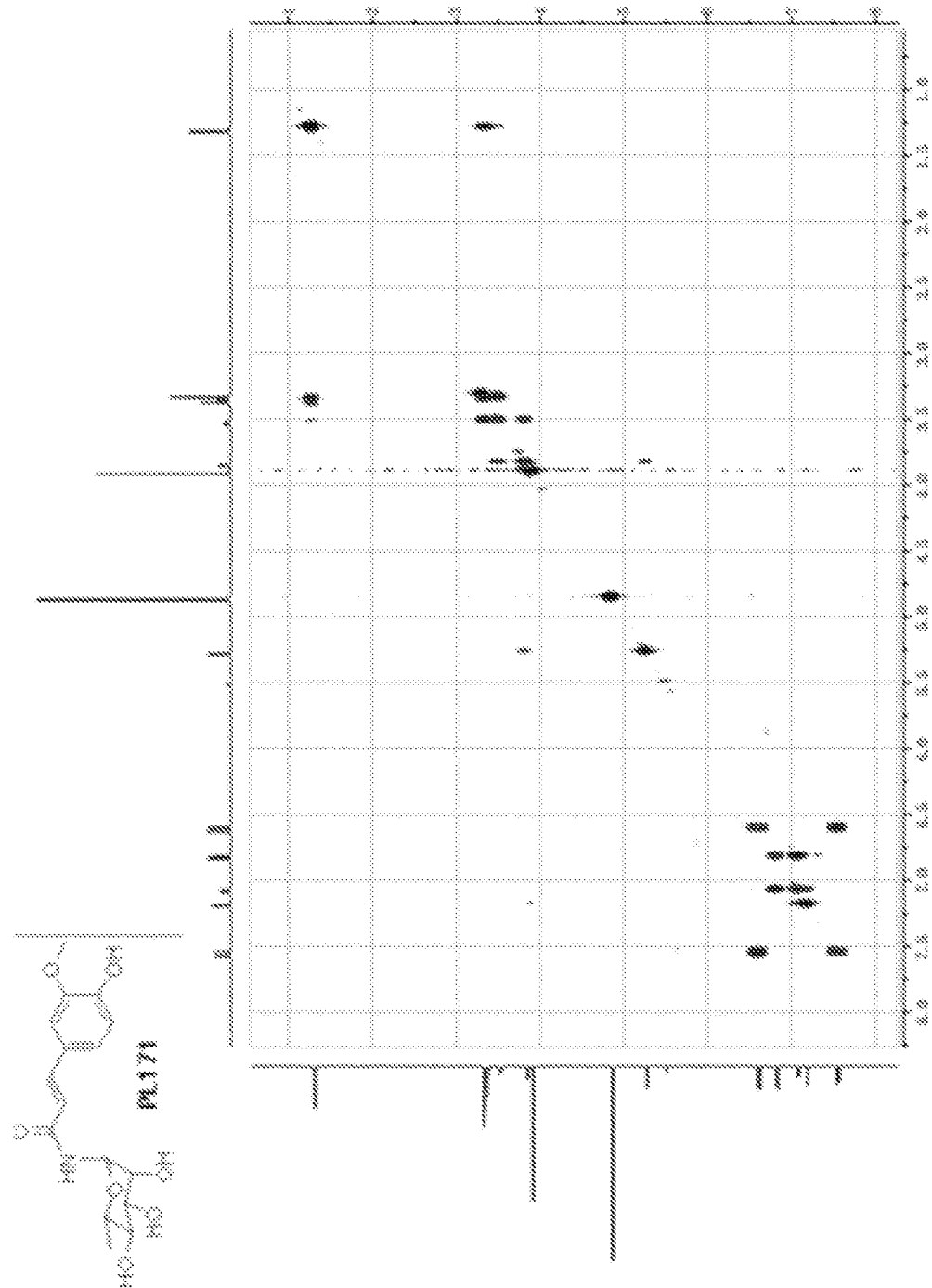
Figure 17:
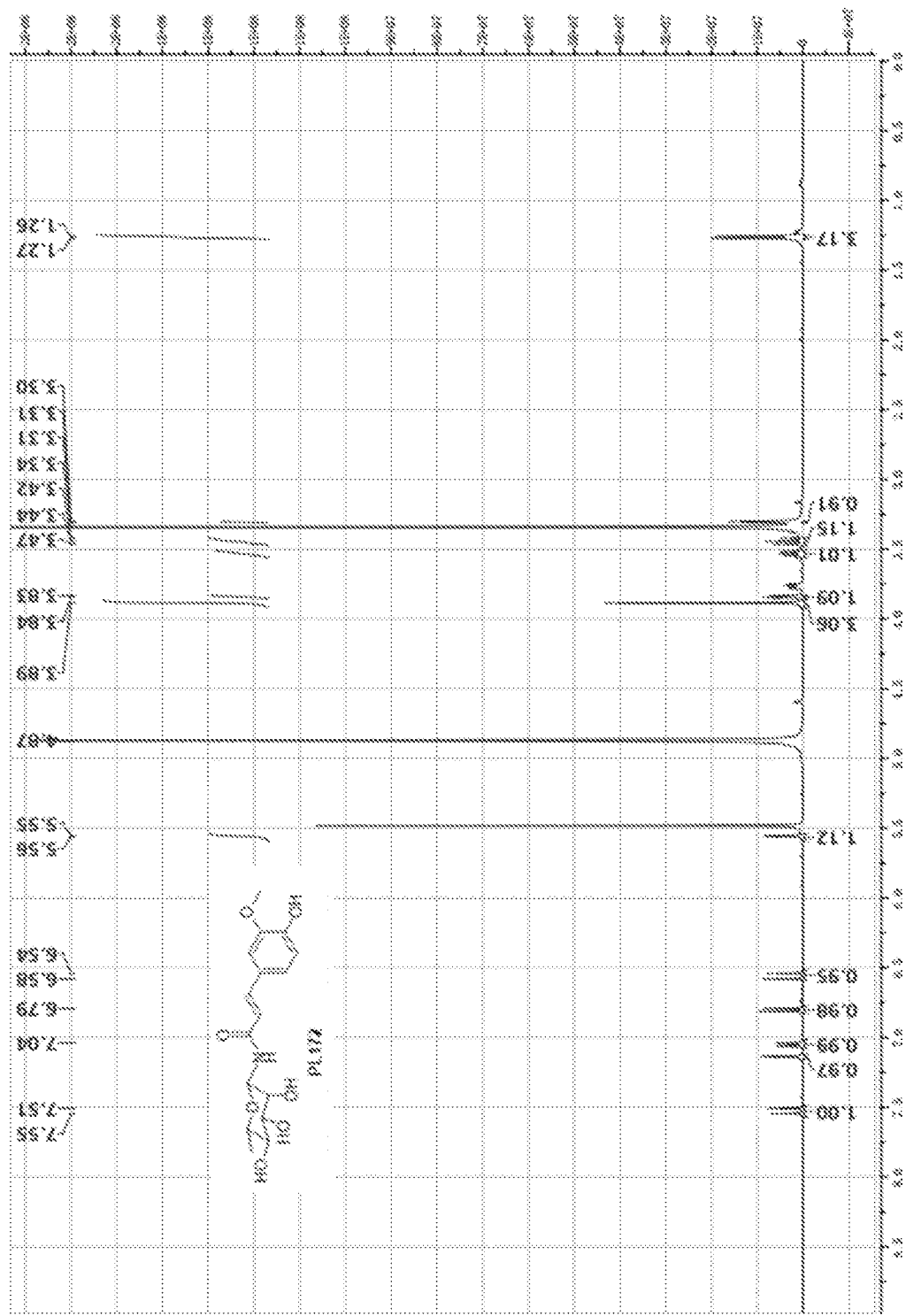
FIG. 17 is the nuclear magnetic resonance spectrum of PL172.

In order to verify the configuration of PL202, 1D NOE experiment was carried out to obtain the 1D NOE spectrum of PL202, which proved that the obtained PL202 was in β configuration, see FIG. 15.

Example 17. Synthesis of PL171

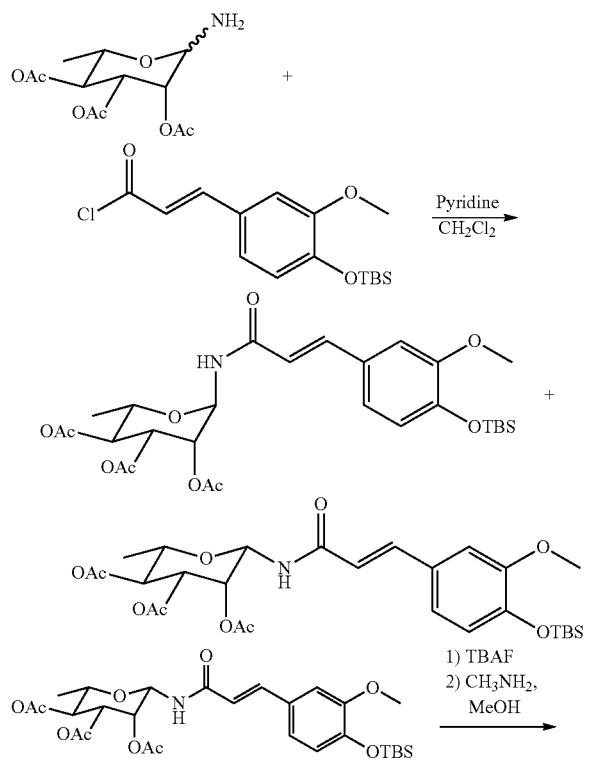

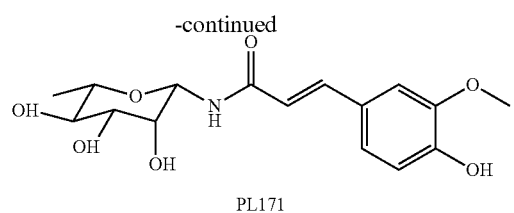

PL171

1-amino-2,3,4-O-triacetyl rhamnose (5.86 g, 19 mmol) was dissolved in 100 mL of anhydrous dichloromethane, and (4-O-TBS)-ferulic acid acyl chloride (6.5 g, 20 mmol) (Free Radical Res. 2015, 102) in anhydrous dichloromethane solution and 1.0 mL of anhydrous pyridine were added dropwise under an ice bath. The reaction was stopped after stirring for 2 hours at room temperature. 200 mL of dichloromethane was added for dilution, then washed with saturated sodium chloride and dried over MgSO$_4$ and concentrated. The β glycosylation product (8.22 g, 70%) and aglycosylation product (1.2 g, 10%) were obtained respectively by column chromatography (petroleum ether:ethyl acetate=10:1 to 2:1). The β glycosylation product (500 mg, 0.86 mmol) was dissolved in dried THF (8.0 mL), the reaction was carried out under the action of TBAF, diluted, washed with saturated sodium chloride, dried over MgSO$_4$ and concentrated to obtain 300 mg of TBS-deprotected product. 300 mg (0.65 mmol) of the resulting product was dissolved in 3.0 mL of dichloromethane, 0.5 mL of 33% CH$_3$NH$_2$ in methanol solution was added dropwise at 0° C., and reacted for 1 hour at 0° C. 70 mg (0.21 mmol) of PL171 was obtained by rapid concentration under reduced pressure and by column chromatography separation (dichloromethane:methanol=20:1 to 6:1). ESI (+)-MS: 340.3 [M+1]$^+$; $^1$H-NMR (CD$_3$OD, 400 MHz) δ 7.56 (d, J=12 Hz, 1H) 7.19 (d, J=4 Hz, 1H), 7.07 (dd, J=6 Hz, J$_2$=1 Hz, 1H), 6.82 (d, J=4 Hz, 1H), 6.62 (d, J=12 Hz, 1H), 5.28 (d, J=1 Hz, 1H), 3.92 (s, 3H), 3.85 (d, J=4 Hz, 1H), 3.54-3.52 (m, 1H), 3.38-3.34 (m, 2H), 1.32 (d, J=4 Hz, 3H).

In order to verify the configuration of PL171, 1D NOE experiment and $^1$H-$^1$H COSY (correlated spectroscopy) experiment were carried out to obtain the 1 D NOE and $^1$H-$^1$H COSY spectrums of PL171, which proved that the obtained PL171 was in β configuration, see FIG. 16.

Example 18. Synthesis of PL72

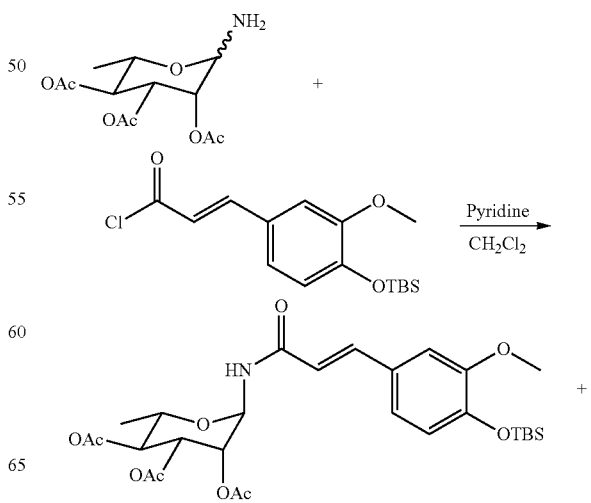

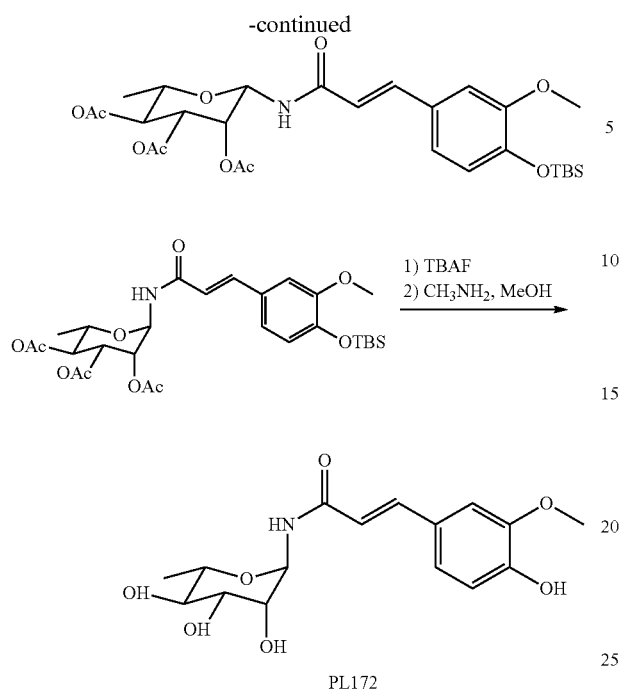

PL172

1-amino-2,3,4-O-triacetyl rhamnose (5.86 g, 19 mmol) was dissolved in 100 mL of anhydrous dichloromethane, and (4-O-TBS)-ferulic acid acyl chloride (6.5 g, 20 mmol) (Free Radical Res. 2015, 102) in anhydrous dichloromethane solution and 1.0 mL of anhydrous pyridine were added dropwise under an ice bath. The reaction was stopped after stirring for 2 hours at room temperature. 200 mL of dichloromethane was added for dilution, then washed with saturated sodium chloride and dried over $MgSO_4$ and concentrated. The β glycosylation product (8.22 g, 70%) and a glycosylation product (1.2 g, 10%) were obtained respectively by column chromatography (petroleum ether:ethyl acetate=10:1 to 2:1). The aglycosylation product (500 mg, 0.86 mmol) was dissolved in dried TI IF (8.0 mL), the reaction was carried out under the action of TBAF, diluted, washed with saturated sodium chloride, dried over $MgSO_4$ and concentrated to obtain 250 mg of TBS-deprotected product. 300 mg (0.54 mmol) of the resulting product was dissolved in 3.0 mL of dichloromethane, 0.5 mL of 33% $CH_3NH_2$ in methanol solution was added dropwise at 0° C., and reacted for 1 hour at 0° C. 45 mg (0.13 mmol) of PL172 was obtained by rapid concentration under reduced pressure and by column chromatography separation (dichloromethane:methanol=20:1 to 6:1). ESI (+)-MS: 340.3 $[M+1]^+$; $^1$H-NMR (CD$_3$OD, 400 MHz) δ 7.53 (d, J=16 Hz, 1H) 7.14 (d, J=4 Hz, 1H), 7.05 (dd, $J_1$=8 Hz, $J_2$=1 Hz, 1H), 6.80 (d, J=8 Hz, 1H), 6.56 (d, J=16 Hz, 1H), 5.56 (d, J=4 Hz, 1H), 3.89 (s, 3H), 3.85-3.83 (m, 1H), 3.54-3.52 (m, 1H), 3.44 (t, J=12 Hz, 1H), 3.31-3.3 (m, 1H) 1.27 (d, J=4 Hz, 3H).

All documents mentioned in this application are hereby incorporated by reference as if each document was individually incorporated by reference. In addition, it should be understood that after reading the above teachings of the invention, those skilled in the art can make various changes or modifications to the invention, and these equivalent forms also fall within the scope defined by the appended claims of this application.

What is claimed is:

1. A compound of formula (I) or a solvate thereof, or their pharmaceutically acceptable salts,

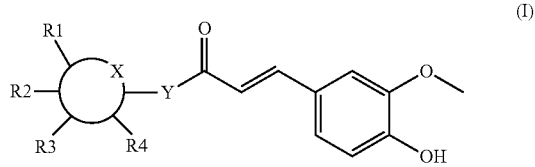

wherein

is a six-membered heterocyclic ring, and X is O;
Y is NH; and
R1 to R4 are each independently selected from hydrogen, hydroxyl, C1 to C4 alkyl, C2 to C4 alkenyl, C2 to C4 alkynyl and halogen.

2. The compound of formula (I) or a solvate thereof, or their pharmaceutically acceptable salts as defined in claim 1, wherein
R1 to R4 are each independently selected from hydrogen, hydroxyl and C1 to C2 alkyl.

3. The compound of formula (I) or a solvate thereof, or their pharmaceutically acceptable salts as defined in claim 1, wherein the compound is as shown in formula IV or V

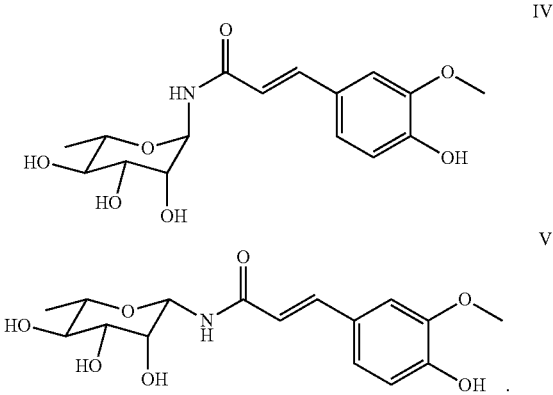

4. A medicament or a medicine kit comprising the compound of formula (I), or a solvate thereof, or their pharmaceutically acceptable salts for alleviating or treating neurodegenerative diseases, depression or stroke,

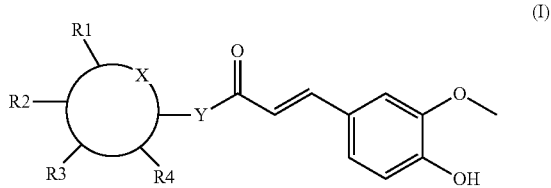

wherein

is a six-membered heterocyclic ring, and X is O;
Y is NH; and
R1 to R4 are each independently selected from hydrogen, hydroxyl, C1 to C4 alkyl, C2 to C4 alkenyl, C2 to C4 alkynyl and halogen.

5. The medicament or the medicine kit as defined in claim 4, wherein the neurodegenerative diseases are
   neurodegenerative diseases characterized by the occurrence of neuroinflammation in the brain; or
   neurodegenerative diseases characterized by a significant increase in Aβ production; or
   neurodegenerative diseases characterized by a significant decline in learning and memory ability; or
   neurodegenerative diseases characterized by a decline in the function of neural stem cells; or
   neurodegenerative diseases characterized by a decline in motor coordination ability; or
   neurodegenerative diseases characterized by a decrease in the number of dopaminergic neurons in Substantia nigra; or
   neurodegenerative diseases characterized by a decrease in the level of striatal dopaminergic nerve fibers.

6. The medicament or the medicine kit as defined in claim 5, wherein the neurodegenerative diseases are selected the group consisting of Alzheimer's disease, Parkinson's disease, dementia with Lewy bodies, Huntington disease and amyotrophic lateral sclerosis.

7. The medicament or the medicine kit as defined in claim 4, wherein the compound of formula (I) is selected the group consisting of compounds as shown in Formulae IV and V

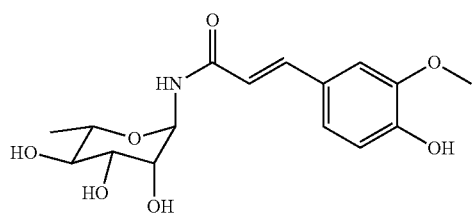

IV

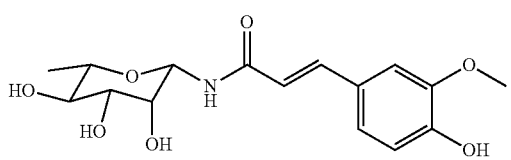

V

8. A composition, comprising the compound of formula (I) or a solvate thereof, or their pharmaceutically acceptable salts for inhibiting neuroinflammation, for improving the function of neural stem cells, for decreasing Aβ production, for increasing the number of dopaminergic neurons in substantia nigra or for increasing the level of striatal dopaminergic nerve fibers,

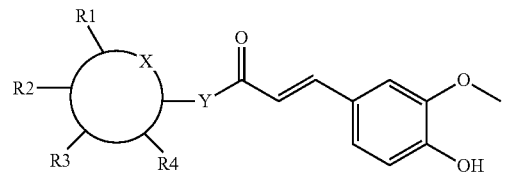

(I)

wherein

is a six-membered heterocyclic ring, and X is O;
Y is NH; and
R1 to R4 are each independently selected from hydrogen, hydroxyl, C1 to C4 alkyl, C2 to C4 alkenyl, C2 to C4 alkynyl and halogen.

9. A pharmaceutical composition, wherein the pharmaceutical composition comprises
   the compound of formula (I) or a solvate thereof, or their pharmaceutically acceptable salts as defined in claim 1; and
   a pharmaceutically acceptable carrier.

10. The pharmaceutical composition as defined in claim 9, wherein the dosage form of the pharmaceutical composition includes a powder, a pulvis, a tablet, a pill, a capsule, a sustained-release preparation, a controlled-release preparation, an injection, an infusion liquid and a suspension.

11. A medicine kit, wherein the medicine kit comprises the compound of formula (I) or a solvate thereof, or their pharmaceutically acceptable salts as defined in claim 1.

12. A method for alleviating or treating neurodegenerative diseases, depression or stroke, wherein the method comprises administering to a subject in need thereof an effective amount of the compound of formula (I) or a solvate thereof, or their pharmaceutically acceptable salts,

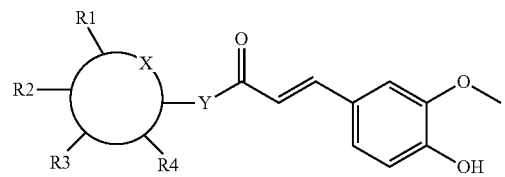

(I)

wherein

is a six-membered heterocyclic ring, and X is O;
Y is selected from O and NH; and
R1 to R4 are each independently selected from hydrogen, hydroxyl, C1 to C4 alkyl, C2 to C4 alkenyl, C2 to C4 alkynyl and halogen.

13. The method as defined in claim 12, wherein the neurodegenerative diseases are
neurodegenerative diseases characterized by the occurrence of neuroinflammation in the brain; or
neurodegenerative diseases characterized by a significant increase in Aβ production; or
neurodegenerative diseases characterized by a significant decline in learning and memory ability; or
neurodegenerative diseases characterized by a decline in the function of neural stem cells; or
neurodegenerative diseases characterized by a decline in motor coordination ability; or
neurodegenerative diseases characterized by a decrease in the number of dopaminergic neurons in Substantia nigra; or
neurodegenerative diseases characterized by a decrease in the level of striatal dopaminergic nerve fibers.

14. The method as defined in claim 13, wherein the neurodegenerative diseases are selected the group consisting of Alzheimer's disease, Parkinson's disease, dementia with Lewy bodies, Huntington disease and amyotrophic lateral sclerosis.

15. The method as defined in claim 12, wherein the compound of formula (I) is selected the group consisting of compounds as shown in Formula II, III, IV and V

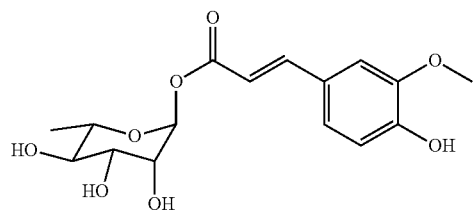
II

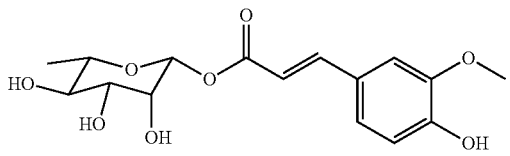
III

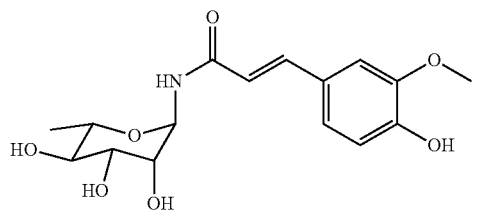
IV

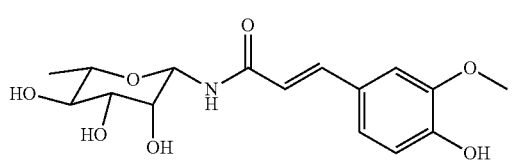
V

16. A method for inhibiting neuroinflammation, for improving the function of neural stem cells, for decreasing Aβ production, for increasing the number of dopaminergic neurons in substantia nigra or for increasing the level of striatal dopaminergic nerve fibers, wherein the method comprises administering to a subject in need thereof an effective amount of the compound of formula (I) or a solvate thereof, or their pharmaceutically acceptable salts

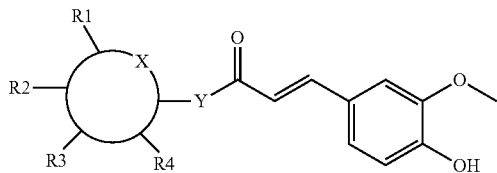
(I)

wherein

is a six-membered heterocyclic ring, and X is O;
Y is selected from O and NH; and
R1 to R4 are each independently selected from hydrogen, hydroxyl, C1 to C4 alkyl, C2 to C4 alkenyl, C2 to C4 alkynyl and halogen.

17. The method as defined in claim 16, wherein the compound of formula (I) is selected the group consisting of compounds as shown in Formula II, III, IV and V

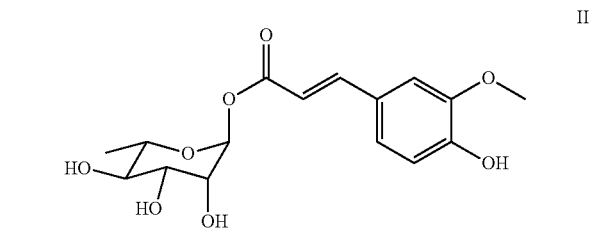 [SMILES: COc1cc(/C=C/C(=O)NC2OC(C)C(O)C(O)C2O)ccc1O]
II

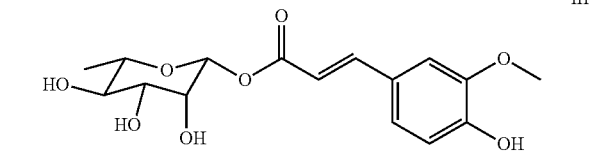
III

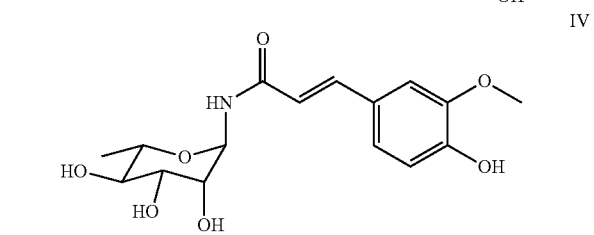
IV

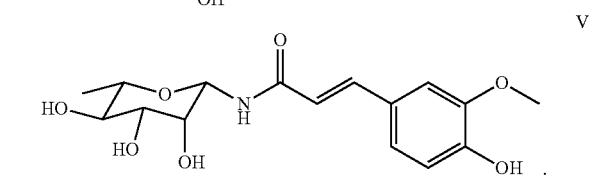
V

18. A method for preparing the compound of Formula III, IV or V, wherein,
the method for preparing the compound of Formula III comprises the step of reacting β rhamnoside with tetra-butyl ammonium fluoride to obtain the compound of Formula III;

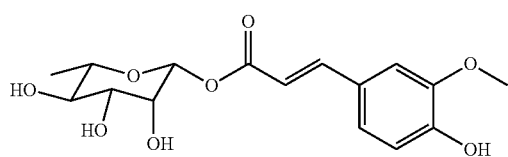

III

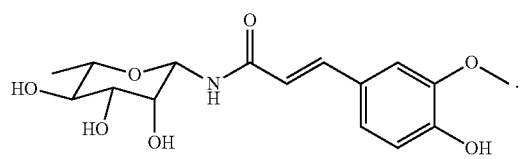

V or, the method for preparing the compound of Formula IV comprises the step of reacting α-1-aminorhamnoside with tetra-butyl ammonium fluoride to obtain the compound of Formula IV;

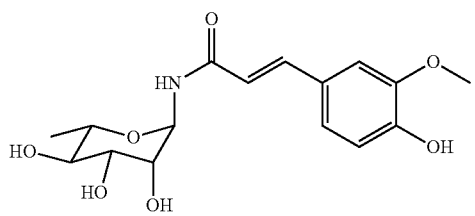

IV or, the method for preparing the compound of Formula V comprises the step of reacting β-1-aminorhamnoside with tetra-butyl ammonium fluoride to obtain the compound of Formula V;

19. A method for preparing the compound of Formula III, IV or V, wherein, in the method for preparing the compound of Formula III, the β rhamnoside is obtained by reacting 2,3,4-O-triacetyl rhamnose with (4-O-tert-butyldimethylsilyl)-ferulic acid acyl chloride;

or, in the method for preparing the compound of Formula IV, the α-1-aminorhamnoside and is obtained by reacting 2,3,4-O-triacetyl-1-aminorhamnose with (4-O-tert-butyldimethylsilyl)-ferulic acid acyl chloride;

or, in the method for preparing the compound of Formula V, the the β-1-aminorhamnosideis is obtained by reacting 2,3,4-O-triacetyl-1-aminorhamnose with (4-O-tert-butyldimethylsilyl)-ferulic acid acyl chloride.

* * * * *